United States Patent
Irisawa et al.

(10) Patent No.: US 11,213,209 B2
(45) Date of Patent: Jan. 4, 2022

(54) DEVICE AND METHOD FOR PROCESSING PHOTOACOUSTIC SIGNAL

(71) Applicant: FUJIFILM Corporation, Tokyo (JP)

(72) Inventors: Kaku Irisawa, Ashigarakami-gun (JP); Kazuhiro Hirota, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1574 days.

(21) Appl. No.: 14/283,662

(22) Filed: May 21, 2014

(65) Prior Publication Data

US 2014/0257079 A1 Sep. 11, 2014

Related U.S. Application Data

(63) Continuation of application No. PCT/JP2012/007492, filed on Nov. 21, 2012.

(30) Foreign Application Priority Data

Nov. 22, 2011 (JP) ............................. JP2011-254654
Nov. 9, 2012 (JP) ............................. JP2012-247099

(51) Int. Cl.
*A61B 5/00* (2006.01)
*G01N 29/46* (2006.01)
(Continued)

(52) U.S. Cl.
CPC ............ *A61B 5/0095* (2013.01); *A61B 5/725* (2013.01); *A61B 5/7257* (2013.01);
(Continued)

(58) Field of Classification Search
None
See application file for complete search history.

(56) References Cited

U.S. PATENT DOCUMENTS

| 5,136,172 A | * | 8/1992 | Nakata | ............... G01N 21/1702 250/559.39 |
| 6,567,688 B1 | * | 5/2003 | Wang | ................... A61B 5/0095 600/407 |

(Continued)

FOREIGN PATENT DOCUMENTS

| JP | 3-156362 A | 7/1991 |
| JP | 9-269370 A | 10/1997 |

(Continued)

OTHER PUBLICATIONS

Decimation (signal processing) by Wikipedia; pub. online on Sep. 13, 2011 at <https://en.wikipedia.org/w/index.php?title=Decimation_(signal_processing)&oldid=450331609>.*

(Continued)

*Primary Examiner* — Katherine L Fernandez
*Assistant Examiner* — Michael S Kellogg
(74) *Attorney, Agent, or Firm* — Birch, Stewart, Kolasch & Birch, LLP

(57) ABSTRACT

To obtain an absorption distribution from a detected signal with a practical device. Light is applied to a subject, and a photoacoustic signal generated in the subjectA photoacoustic is detected. From the detected photoacoustic signal, a light differential waveform, which is a differential waveform of a temporal waveform of the light applied to the subject, is deconvolved. As a result of this deconvolution, an absorption distribution is obtained.

19 Claims, 15 Drawing Sheets

(51) Int. Cl.
*G01N 29/24* (2006.01)
*G01N 29/06* (2006.01)
*A61B 8/00* (2006.01)

(52) U.S. Cl.
CPC ....... *A61B 8/4416* (2013.01); *G01N 29/0654* (2013.01); *G01N 29/2418* (2013.01); *G01N 29/46* (2013.01); *A61B 5/0093* (2013.01); *A61B 5/7278* (2013.01); *G01N 2291/02475* (2013.01)

(56) References Cited

U.S. PATENT DOCUMENTS

| 7,322,972 B2 * | 1/2008 | Viator | A61B 18/203 606/9 |
|---|---|---|---|
| 2005/0187471 A1 * | 8/2005 | Kanayama | A61B 5/0091 600/437 |
| 2007/0197886 A1 * | 8/2007 | Naganuma | A61B 5/0095 600/322 |

FOREIGN PATENT DOCUMENTS

| JP | 2010-167167 A | 8/2010 |
|---|---|---|
| JP | 2010-167258 A | 8/2010 |
| JP | 2011-120795 A | 6/2011 |
| WO | WO 2010/074104 A1 | 7/2010 |
| WO | WO 2011/070985 A1 | 6/2011 |

OTHER PUBLICATIONS

Upsampling by Wikipedia; pub. online on Nov. 4, 2011 at <https://en.wikipedia.org/w/index.php?title=Upsampling&oldid=459014652>.*

Discrete-time Fourier transform by Wikipedia; pub. online on Dec. 10, 2011 at <https://en.wikipedia.org/w/index.php?title=Discrete-time_Fourier_transform&oldid=465128520>.*

Fast Fourier transform by Wikipedia; pub. online on Dec. 7, 2011 at <https://en.wikipedia.org/w/index.php?title=Fast_Fourier_transform&oldid=464516132>.*

LG. Calasso et al., "Photoacoustic Point Source", Physical Review Letters, vol. 86, No. 16, pp. 3550-3553, Apr. 16, 2001.

International Search Report, dated Mar. 19, 2013, issued in PCT/JP2012/007492.

Y. Wang et al., "Photoacoustic imaging with deconvolution algorithm", Physics in Medicine and Biology, vol. 49, pp. 3117-3124, 2004.

Y.Xu et al., "Exact Frequency-Domain Reconstruction for Thermoacoustic Tomography—I: Planar Geometry", IEEE Transactions on Medical Imaging, vol. 21, No. 7, pp. 823-828, Jul. 2002.

* cited by examiner

PHOTOACOUSTIC SIGNAL AFTER RECONSTRUCTION
(ABSCISSA AXIS μsec)

RECIPROCAL OF LIGHT PULSE DIFFERENTIAL
WAVEFORM FFT (ABS) (ABSCISSA AXIS  MHz)
(LIGHT PULSE DIFFERENTIAL WAVEFORM FFT FILTER)

FFT WAVEFORM AFTER DECONVOLUTION (ABS)
(ABSCISSA AXIS : MHz)

PHOTOACOUSTIC WAVEFORM
AFTER DECONVOLUTION (ABSCISSA AXIS : μsec)
(ABSORPTION DISTRIBUTION SIGNAL)

PRESSURE DISTRIBUTION IMAGE

ABSORPTION DISTRIBUTION IMAGE

LIGHT PULSE DIFFERENTIAL WAVEFORM

LIGHT PULSE DIFFERENTIAL WAVEFORM

DEVICE AND METHOD FOR PROCESSING PHOTOACOUSTIC SIGNAL

CROSS-REFERENCE TO RELATED APPLICATIONS

This application is a Continuation of PCT International Application No. PCT/JP2012/007492 filed on Nov. 21, 2012, which claims priority under 35 U.S.C § 119(a) to Japanese Patent Application No. 2011-254654 filed on Nov. 22, 2011 and Japanese Patent Application No. 2012-247099 filed on Nov. 9, 2012. Each of the above applications is hereby expressly incorporated by reference, in its entirety, into the present application.

TECHNICAL FIELD

The present invention relates to a device and a method for processing photoacoustic signals, and more particularly to a device and a method for processing photoacoustic signals that are generated in a subject due to light applied to the subject.

BACKGROUND ART

Ultrasonography is known as one of imaging examination methods that allow non-invasive examination of the state of the interior of a living body. In ultrasonography, an ultrasound probe that can transmit and receive ultrasound is used. Ultrasound transmitted from the ultrasound probe to the subject (living body) travels through the interior of the living body and is reflected at a tissue interface. Then, the reflected ultrasound is received by the ultrasound probe. Based on the time taken for the reflected ultrasound to return to the ultrasound probe, the distance is calculated, thereby imaging the state of the interior.

Further, photoacoustic imaging, which images the interior of a living body using the photoacoustic effect, is known. In photoacoustic imaging, in general, pulsed laser light is applied to the interior of a living body. In the interior of the living body, a living tissue, for example, absorbs energy of the pulsed laser light and ultrasound (a photoacoustic signal) is generated due to adiabatic expansion caused by the energy. This photoacoustic signal is detected using an ultrasound probe, or the like, and a photoacoustic image is constructed based on the detected signal, thereby visualizing the interior of the living body based on the photoacoustic signal.

With a usual reconstruction method (such as a Fourier domain method (FTA method) or a delay-and-sum method), substantially a pressure distribution is imaged, and the generated photoacoustic image is not a distribution image of light-absorbing substances. In a photoacoustic image that images a pressure distribution, one blood vessel may be shown doubled. This phenomenon can be explained as follows. Assuming that a pressure waveform generated by a micro element (micro absorptive substance) is a micro waveform, a pressure waveform generated by a blood vessel, which is a macro structure, can be understood as superposition of micro waveforms. As the micro waveforms generated at micro absorptive substances are superposed, the micro pressure waveforms generated in the interior of the blood vessel are superposed with adjacent micro waveforms and cancelled. When all the micro pressure waveforms from the blood vessel are superposed, finally part of the pressure waveforms generated at the front side of the blood vessel (anterior edge) and part of the pressure waveforms generated at the rear side (posterior edge) remain without being cancelled, and these pressure waveforms are observed. Thus, the blood vessel is shown doubled. When one blood vessel is shown doubled, it is difficult to check the position of the blood vessel during image interpretation. Further, when images obtained at different wavelengths are calculated, there is high tendency of positional misalignment and appropriate results may not be obtained.

In place of generating the pressure distribution image, some techniques for generating an absorption distribution image are known. For example, Japanese Unexamined Patent Publication No. 3 (1991)-156362 (hereinafter, Patent Document 1) teaches that an inverse filter for restoring degraded resolution of a photoacoustic image is calculated from a thermal impulse response of a sample, and the inverse filter is applied to an obtained photoacoustic image to obtain an ideal photoacoustic image, namely, thermal impedance information (=a set of infinitesimal point light sources) at points (infinitesimal) on the surface of the sample excited by point light sources and detected.

More specifically, in Patent Document 1, first, a thermal impulse response h(x,y) of the sample is calculated, and then a photoacoustic image p(x,y) is constructed. The thermal impulse response is defined as a transfer function of a temperature change at an infinitesimal point being converted into a micro displacement on the surface of the sample. Thereafter, the thermal impulse response h(x,y) and the photoacoustic image p(x,y) are respectively subjected to a Fourier transform to provide Fourier transformed images $H(\mu,\upsilon)$ and $P(\mu,\upsilon)$. Using $1/H(\mu,\upsilon)$ as the inverse filter, $Q(\mu,\upsilon)$ is calculated as follows:

$$Q(\mu,\upsilon)=P(\mu,\upsilon)\cdot(1/H(\mu,\upsilon)).$$

By applying an inverse Fourier transform to the thus calculated $Q(\mu,\upsilon)$, an ideal photoacoustic image q(x,y) can be obtained.

Besides the above-mentioned Patent Document, Y. Xu et al., "Exact Frequency-Domain Reconstruction for Thermoacoustic Tomography-I: Planar Geometry", IEEE TRANSACTIONS ON MEDICAL IMAGING, Vol. 21, No. 7, pp. 823-828, 2002 (hereinafter, Non-Patent Document 1), teaches as a logic that, assuming that a Fourier transform of a light pulse η(t) having a finite duration is η(k), a differential iη(k) thereof is taken into account. As an experiment, a microwave having a pulse duration that is long enough for an excitation light pulse waveform to be within the detection band of PZT (lead zirconate titanate), which is a detection element, is applied to the subject, and a photoacoustic signal is detected with a usual PZT probe to reconstruct the absorption distribution.

Y. Wang et al., "Photoacoustic imaging with deconvolution algorithm", Physics in Medicine and Biology, Vol. 49, pp. 3117-3124, 2004 (hereinafter, Non-Patent Document 2), teaches that a micro waveform (as a pressure waveform from a micro element in the subject) that is a combination of a light pulse differential function and a device impulse response function, and an absorption distribution distribution are associated with an observed pressure waveform. Reconstruction of the absorption image is achieved by measuring $p_{d0}$ that contains a light differential and a system response in an inseparable manner, deconvolving the $p_{d0}$ from a pressure waveform of each element, and then using a filtered back projection method. As an experiment, pulsed laser light with a short pulse duration is used for excitation, and a photoacoustic signal is detected using a hydrophone and an oscilloscope with an ultrasound detection band wider than that of a usual ultrasound diagnostic device to reconstruct the absorption distribution.

DISCLOSURE OF INVENTION

In Non-Patent Document 1, the Fourier transformed light pulse η(k) is not handled as a position-dependent function η(r, k). Therefore, when a pressure distribution at t=0 can be reconstructed (that is, an estimation backward in time of a pressure distribution that is generated at the moment when light entered (t=0) can be calculated based on the detected waveform), an accurate absorption distribution can be obtained. However, if a pressure distribution at t≠0 is reconstructed (that is, a pressure distribution at the moment when light entered (t=0) cannot be reconstructed and a pressure distribution after a while from the clock time t=0 is estimated), light pulse duration components cannot be removed and only a pressure distribution is obtained.

In Non-Patent Documents 1 and 2, reconstruction is performed by aligning a laser emission time and an ultrasound detection time by setting one of the excitation laser and the ultrasound detection device out of a practical range. Therefore, although there is no problem clearly appearing in Non-Patent Documents 1 and 2, when a practical device configuration is assumed, it is difficult to reconstruct the pressure distribution at t=0 by the methods of Non-Patent Documents 1 and 2. Namely, in a case where an ultrasound detection device using a narrow band probe utilizing PZT, or the like, with a sampling frequency of not more than 100 MHz, and an excitation laser having a light pulse duration on the order of 1-100 ns for outputting a strong photoacoustic signal are used as a practical device configuration, for example, the laser emission is a short time phenomenon when compared to the ultrasound detection time, and therefore accurate reconstruction of the state corresponding to t=0 (which is a time at which the absorption distribution is proportional to the pressure distribution) cannot be achieved.

It should be noted that a "pressure distribution at the clock time t=0" represents the "absorption distribution". Therefore, if the pressure distribution at the clock time t=0 can be found, the absorption distribution can be obtained. However, a sampling interval of a typical ultrasound detection device is around 25 ns, and therefore if one attempts to perform the reconstruction at the clock time t=0, which is the moment when light entered, there is actually a time lag of about t=±12.5 ns. For example, in a case where the light pulse duration is as long as 100 ns, the time lag (±12.5 ns) can be considered as an error; whereas in a case where the light pulse duration is 10 ns, the time lag can no longer be considered as an error, and the state transitions into a pressure distribution in the course of propagation of a pressure wave, rather than a pressure distribution at the moment when light entered. The "pressure distribution in the course of propagation of a pressure wave" does not coincide with the "absorption distribution".

Further, with a sample such as an experimental living body, it is difficult to define the pressure distribution at t=0. Assuming that a speed of sound in a living body is 1530 m/s, for example, and a difference between a detection clock time and a laser application clock time is a propagation time, then a propagation distance can be calculated from the propagation time. If the speed of sound in the living body is 1530 m/s and constant, the propagation distance calculated from the propagation time is equal to the actual propagation distance. However, actually the speed of sound is not uniform in the living body and there is a difference between the calculated propagation distance and the actual propagation distance. Therefore, in the case where the propagation distance is estimated from the detected signal, ambiguity of the propagation distance due to differences of the speed of sound remains. When the ambiguity of the propagation distance in a living body is regarded as ambiguity of the propagation time, the clock time t=0 also has ambiguity, and the pressure distribution at t=0 is also ambiguous and it is difficult to define it. The distribution at t=0 is the absorption distribution, whereas the distribution at t>0 is a pressure distribution during propagation. When these distributions are mixed, it is no longer deemed to be the absorption distribution.

In view of the above-described circumstances, the present invention is directed to providing a photoacoustic signal processing device and a photoacoustic signal processing method which allow calculating an absorption distribution from a detected signal with a practical device.

In order to solve the above-described problem, the invention provides a photoacoustic signal processing device including: sampling means for sampling a photoacoustic signal generated in a subject due to light applied to the subject; and light differential waveform deconvolution means for generating, from the sampled photoacoustic signal, a signal from which a light differential waveform is deconvolved, the light differential waveform being a differential waveform of a temporal waveform of light intensity of the light applied to the subject.

The photoacoustic signal processing device of the invention may further include light differential waveform obtaining means for obtaining the differential waveform of the temporal waveform of light intensity of the light applied to the subject.

In the invention, the light differential waveform deconvolution means may include first Fourier transform means for applying a Fourier transform to the sampled photoacoustic signal; second Fourier transform means for applying a Fourier transform to a signal obtained by sampling the light differential waveform at a predetermined sampling rate; inverse filter calculation means for calculating, as an inverse filter, a reciprocal of the Fourier transformed light differential waveform; filter application means for applying the inverse filter to the Fourier transformed photoacoustic signal; and inverse Fourier transform means for applying an inverse Fourier transform to the photoacoustic signal processed with the inverse filter.

The photoacoustic signal may be sampled at a first sampling rate and the light differential waveform may be sampled at a second sampling rate that is higher than the first sampling rate, the photoacoustic signal processing device may further include resampling means for resampling at the second sampling rate the photoacoustic signal sampled at the first sampling rate, and the first Fourier transform means may apply a Fourier transform to the photoacoustic signal resampled by the resampling means. In this case, the first Fourier transform means and the second Fourier transform means may apply a Fourier transform of the same number of data points.

Alternatively, the photoacoustic signal may be sampled at a first sampling rate, the light differential waveform may be sampled at a second sampling rate higher than the first sampling rate, the first Fourier transform means may perform a Fourier transform of a first number of data points, and the second Fourier transform means may perform a Fourier transform of a second number of data points greater than the first number of data points, the photoacoustic signal processing device may further include zero padding means for performing, on the Fourier transformed photoacoustic signal, zero padding to add 0's of a number corresponding to a difference between the first number of data points and the second number of data points at the center of the Fourier transformed photoacoustic signal, and the filter application means may apply the inverse filter to a zero-padded signal provided by the zero padding means.

Still alternatively, the photoacoustic signal may be sampled at a first sampling rate, the light differential waveform may be sampled at a second sampling rate higher than the first sampling rate, the first Fourier transform means may perform a Fourier transform of a first number of data points, and the second Fourier transform means may perform a Fourier transform of a second number of data points greater than the first number of data points, the photoacoustic signal processing device may further include high frequency component sample point removal means for removing, from the Fourier transformed light differential waveform, high frequency component sample points of a number corresponding to a difference between the first number of data points and the second number of data points, and the inverse filter calculation means may calculate, as the inverse filter, a reciprocal of a signal obtained by removing the high frequency component sample points from the Fourier transformed light differential waveform.

The second number of data points may be equal to or greater than a number of data points calculated by multiplying the first number of data points by a ratio of the second sampling rate to the first sampling rate.

It is preferred that the photoacoustic signal processing device of the invention further includes photoacoustic signal reconstruction means for reconstructing a photoacoustic signal that is detected with a plurality of detector elements and sampled by the sampling means based on the photoacoustic signal, wherein the light differential waveform deconvolver deconvolves the light differential waveform from the reconstructed photoacoustic signal reconstructed by the photoacoustic signal reconstruction means.

The photoacoustic signal processing device may further include correcting means for correcting the signal from which the light differential waveform is deconvolved such that influence of reception angle-dependent properties of a detector detecting the photoacoustic signal is removed from the signal from which the light differential waveform is deconvolved.

The correcting means may correct the signal from which the light differential waveform is deconvolved such that, in place of or in addition to the reception angle-dependent properties of the detector, influence of an incoming light distribution on the subject is removed from the signal from which the light differential waveform is deconvolved.

The light differential waveform deconvolution means may further filter a noise-amplified frequency band when it performs the deconvolution.

In the invention, the light applied to the subject may include a plurality of wavelengths of light, the sampling means may sample a photoacoustic signal corresponding to light of each wavelength, and the light differential waveform deconvolution means may generate, from the photoacoustic signal corresponding to the light of each wavelength, a signal from which the light differential waveform is deconvolved, and, in this case, the photoacoustic signal processing device may further include two-wavelength data calculation means for calculating, from the photoacoustic signal corresponding to the light of each wavelength, a signal from which the light differential waveform is deconvolved.

The photoacoustic signal processing device of the invention may further include photoacoustic image generating means for generating a photoacoustic image based on the signal from which the light differential waveform is deconvolved.

The sampling means may further sample a reflected acoustic wave of an acoustic wave transmitted to the subject, and the photoacoustic signal processing device may further include: reflected acoustic wave image generating means for generating a reflected acoustic wave image based on the sampled reflected acoustic wave; and image combining means for combining the photoacoustic image with the reflected acoustic wave image.

The image combining means may combine the images by superimposing the photoacoustic image and the reflected acoustic wave image one on the other.

The present invention also provides a photoacoustic signal processing method including the steps of: detecting a photoacoustic signal generated in a subject due to light applied to the subject; and deconvolving, from the detected photoacoustic signal, a light differential waveform, which is a differential waveform of a temporal waveform of light intensity of the light applied to the subject.

In the photoacoustic signal processing device of the invention, the step of deconvolving may include the steps of: applying a Fourier transform to the detected photoacoustic signal; applying a Fourier transform to the light differential waveform; calculating, as an inverse filter, a reciprocal of the Fourier transformed light differential waveform; applying the inverse filter to the Fourier transformed photoacoustic signal; and applying an inverse Fourier transform to the photoacoustic signal processed with the inverse filter.

In the device and method for processing photoacoustic signals of the invention, a light differential waveform, which is a differential of a temporal waveform of light intensity of the light applied to the subject, is deconvolved from a photoacoustic signal generated in the subject. With this, a light differential term can be removed from the detected signal in which the light differential term is convolved, thereby allowing calculating an absorption distribution from the detected signal. By imaging such an absorption distribution, a photoacoustic image representing an absorption distribution image can be obtained.

DESCRIPTION OF PREFERRED EMBODIMENTS

Figure 1:
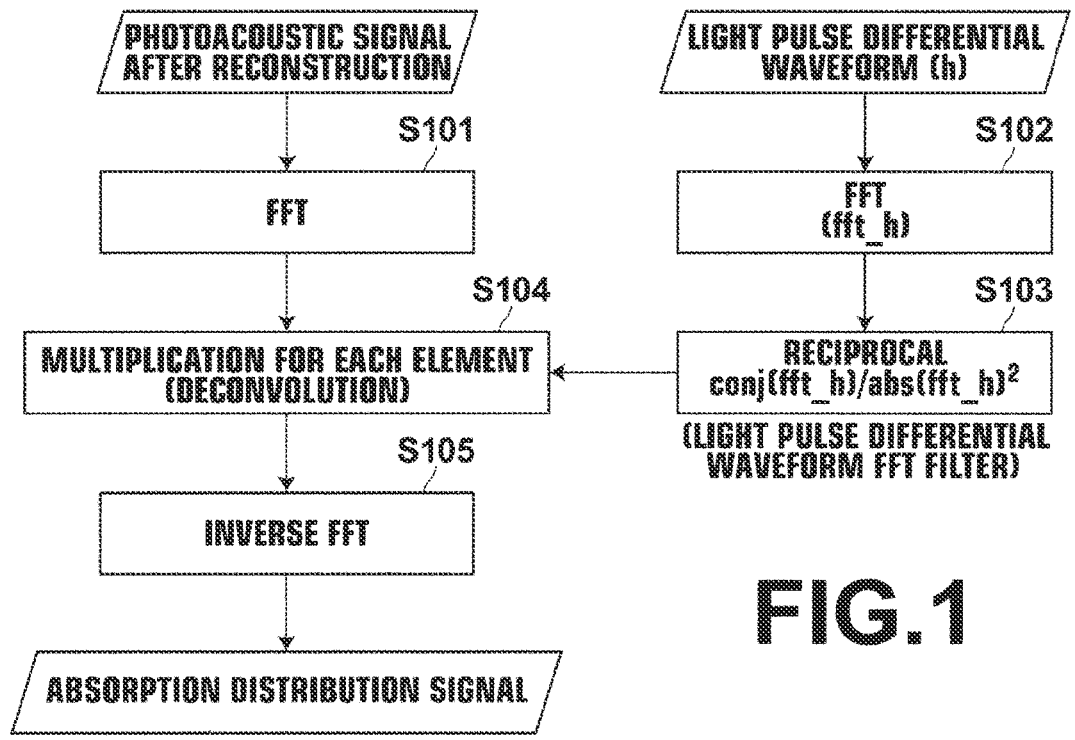
FIG. 1 is a block diagram illustrating the basic algorithm of light pulse differential waveform deconvolution.

Prior to describing embodiments of the present invention, the outline of the invention is described. It is assumed here that micro absorptive particles, which are light-absorbing substances, absorb pulsed laser light and a pressure wave (photoacoustic pressure wave) is generated. According to [I. G. Calasso et al., "Photoacoustic Point Source", PHYSICAL REVIEW LETTERS, Vol. 86, No. 16, pp. 3550-3553, 2001], a pressure waveform $p_{micro}(R,t)$, which is a photoacoustic pressure wave generated by a micro absorptive particle at a position r and observed at a position R at a clock time t, is a spherical wave of the equation below:

$$p_{micro}(R, t) = \frac{k}{|r-R|} \frac{d}{d\left(t - \frac{|r-R|}{v_s}\right)} I\left(t - \frac{|r-R|}{v_s}\right),$$

where I(t) is a temporal waveform of light intensity of the excitation light, the coefficient k is a conversion factor when the particle absorbs light and outputs the acoustic wave, and $v_s$ is a speed of sound in the subject. Each of the positions r and R is a vector representing a spatial position. As shown by the equation above, the pressure generated by the micro absorptive particles is a spherical wave that is proportional to a light pulse differential waveform.

A pressure waveform obtained from an actual object to be imaged has a size of a more macro absorptive substance, and therefore is assumed to be a waveform formed by superposing the above-described micro absorption waveforms (the superposition principle). It is assumed here that an absorption distribution of particles that generate a macro photoacoustic wave is A(r–R), and an observed waveform of the pressure from the macro absorptive substance is $p_{macro}(R, t)$. At the observation position R, a photoacoustic wave from an absorptive particle located at a radius $v_s t$ from the observation position R is observed at each clock time. Therefore, the observed waveform $p_{macro}(R,t)$ is expressed as the pressure waveform equation below:

$$p_{macro}(R, t) = \int\int\int A(r-R) \times \tag{1}$$

$$\frac{k}{|r-R|} \frac{d}{d\left(t - \frac{|r-R|}{v_s}\right)} I\left(t - \frac{|r-R|}{v_s}\right) dV$$

$$= \int_0^\pi \int_{-\frac{\pi}{2}}^{\frac{\pi}{2}} \int_0^{|r-R|=v_s t} \frac{kA(r-R)}{|r-R|} I'\left(t - \frac{|r-R|}{v_s}\right)$$

$$|r-R|^2 \sin\theta d|r-R| d\theta d\phi$$

$$= \int_0^{|r-R|=v_s t} \frac{k}{|r-R|} \int_0^\pi \int_{-\frac{\pi}{2}}^{\frac{\pi}{2}} A(r-R) dS \times$$

$$I'\left(t - \frac{|r-R|}{v_s}\right) d|r-R|$$

$$= \left[\frac{k}{|r-R|} \int_0^\pi \int_{-\frac{\pi}{2}}^{\frac{\pi}{2}} A(r-R) dS\right] * \left[I'\left(t - \frac{|r-R|}{v_s}\right)\right]$$

As can be seen from the equation (1) above, the observed waveform shows a convolution type of light pulse differential.

In Non-Patent Document 2, based on an equation where a device impulse response is further convolved in the above-described equation, it is proposed to deconvolve the $p_{d0}$, which contains a light differential and a system response in an inseparable state, from the observed waveform $p_{macro}$, and then reconstruct the absorption distribution A(r–R) using filtered back projection. In Non-Patent Document 2, it is emphasized to take the device impulse response into account rather than the influence of the light, pulse differential. Therefore, even a frequency band where a sufficient S/N ratio (Signal to Noise Ratio) for the device is not achieved is emphasized, resulting in increase of image noise after the processing. Therefore, in Non-Patent Document 2, it is necessary to include a high frequency filter in the processing.

In the case where a wide-band ultrasound probe is used, as in Non-Patent Document 2, the above-described method may be sufficient. However, in the case where a practical narrow-band probe is used, the frequency of the ultrasound signal to be detected is low relative to the device impulse response, and therefore the band of a waveform to be deconvolved is wide relative to the signal (low frequency) detected with a usual ultrasound probe and appropriate deconvolution cannot be achieved, resulting in a failure image. What is important in obtaining the absorption distribution is taking the light pulse differential term into account. In deconvolution processing of the invention, the deconvolution is performed with taking only the light pulse differential term into account.

Further, in the invention, the present inventors have considered applying reconstruction (such as a FTA method, a DnS method or a BP method) for calculating a pressure distribution, which is also used in a conventional ultrasound system, and then converting the reconstructed image into an absorption distribution with recognizing that the reconstructed image is a pressure distribution at t≠0, i.e., a pressure distribution in the course of propagation of the pressure wave. As the basic idea of the reconstruction of a pressure distribution, a pressure distribution $p_{rec}(R, t)$ after reconstruction for a detection position R=(x, y,0) is obtained by summing a spherical wave (a detection signal thereof) generated from an absorptive substance located at a position |r–R| along an axis of detection (r–R) of the R at each clock time t and signals from piezoelectric devices around the absorptive substance (along the detection axis) to calculate a pressure intensity at the position. Therefore, $p_{rec}(R, t)$ which is obtained by superposing photoacoustic waves generated and propagate from the micro absorptive substances present along the axis of detection (r–R), is expressed as follows:

$$p_{rec}(R, t) = \int A(|r-R|) \times \frac{k}{|r-R|} I'\left(t - \frac{|r-R|}{v_s}\right) d|r-R| \quad (2)$$

When the absorption distribution can be handled one-dimensionally in this manner, the pressure can be expressed as the above-shown equation. Assuming that the axis of detection (r–R) is the z-axis and the distance |r–R| from the detector element is z, the equation (2) above can be expressed as follows:

$$p_{rec}\left(x, y, t\left(=\frac{z'}{v_s}\right)\right) = \int A(x, y, z)\frac{k}{z} \times I'\left(t - \frac{z}{v_s}\right) dz \quad (3)$$

Further, by omitting x and y that are not related to the integration in the equation (3) and expressing the z-axis in time, the above equation can be expressed as follows:

$$p_{rec}\left(x, y, t\left(=\frac{z'}{v_s}\right)\right) = \frac{kA(v_s t)}{v_s t} * I'(t) \quad (4)$$

In this manner, the single-axis (time axis or z' axis) expression of convolution for the detector element located at (x,y,0) can be achieved.

By applying a Fourier transform to both sides of the above equation (4) and dividing the Fourier coefficient of the pressure distribution by the Fourier coefficient of the time differential of the light pulse along the frequency axis, deconvolution of the light pulse differential can be achieved.

$$F\left\{p_{rec}\left(t\left(=\frac{z'}{v_s}\right)\right)\right\} = F\left\{\frac{kA(v_s t)}{v_s t}\right\} F\left\{\frac{d}{dt}I(t)\right\} \Rightarrow F\left\{\frac{kA(v_s t)}{v_s t}\right\}$$
$$= \frac{F\left\{p_{rec}\left(t\left(=\frac{z'}{v_s}\right)\right)\right\}}{F\left\{\frac{d}{dt}I(t)\right\}}$$

After the deconvolution, an inverse Fourier transform is applied to the obtained equation to find $A(x,y,v_s t)$, thereby imaging the absorption distribution. In the thus found $A(x, y,v_s t)$, reception angle dependence $D(x,y,z)$ of the detector element and a natural vibration of the probe band may possibly be convolved. For example, influence of the reception angle dependence of the detector element can be removed by multiplying $A(x,y,v_s t)$ by a reciprocal of the instrumental function $D(x,y,z)$, which is calculated in advance. Also, influence of the natural vibration of the band can be removed by converting the image into an intensity image using a Hilbert transform or quadrature detection. Further, a spatial distribution $L(x,y,z)$ of the light entering the sample may be separately found through observation or simulation, and a pixel value $\mu(x,y,z)$ that is proportional to the absorption coefficient may be calculated by the equation:

$$\mu(x,y,z) = A(x,y,v_s t)/L(x,y,z).$$

In this case, a distribution image of the absorption coefficient, which is a physical quantity more closely related to a living body tissue, can be obtained.

Figure 2A:
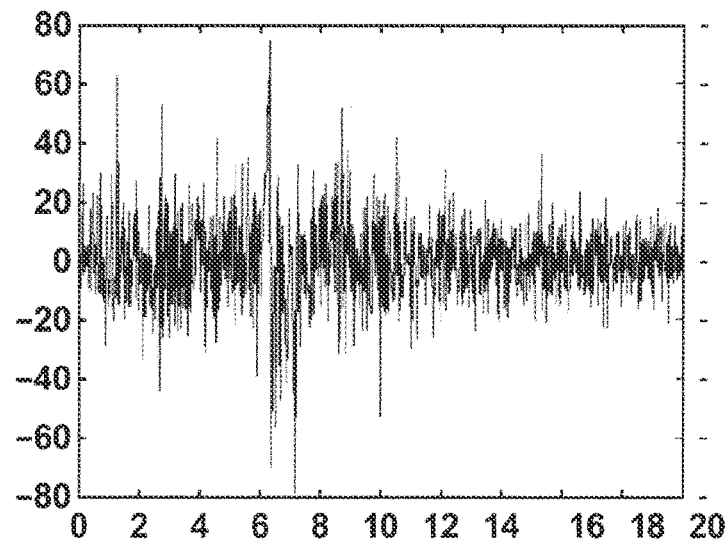
FIG. 2A is a waveform chart showing a photoacoustic signal after reconstruction.
Figure 2B:
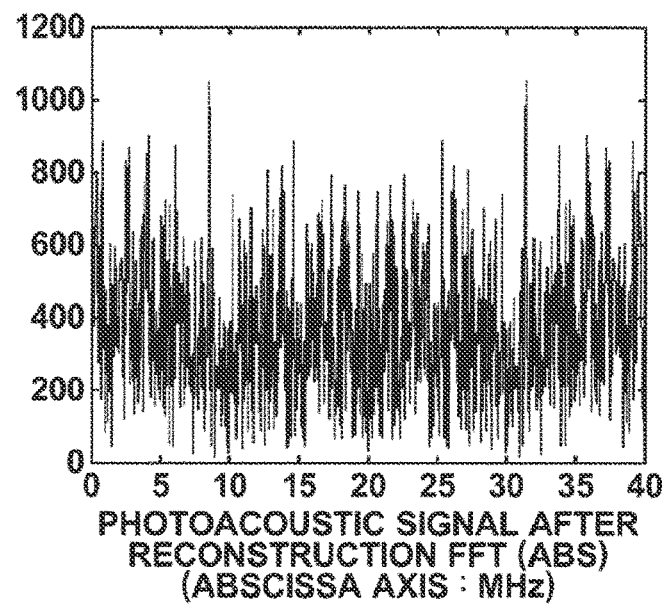
FIG. 2B is a waveform chart showing a photoacoustic signal FFT after FFT.

FIG. 1 shows the basic algorithm of light pulse differential waveform deconvolution. A photoacoustic signal after reconstruction is inputted, and the photoacoustic signal after reconstruction is subjected to a Fourier transform using FFT (Fast Fourier transform) (step S101). FIG. 2A shows a photoacoustic signal after reconstruction, and FIG. 2B shows the photoacoustic signal FFT after FFT. By applying the Fourier transform to the time domain signal, as shown in FIG. 2A, the time domain signal is converted into the frequency domain signal, as shown in FIG. 2B. It should be noted that, although FIG. 2B shows absolute values of the photoacoustic signal FFT, complex numbers are handled in the actual processing.

Figure 2C:
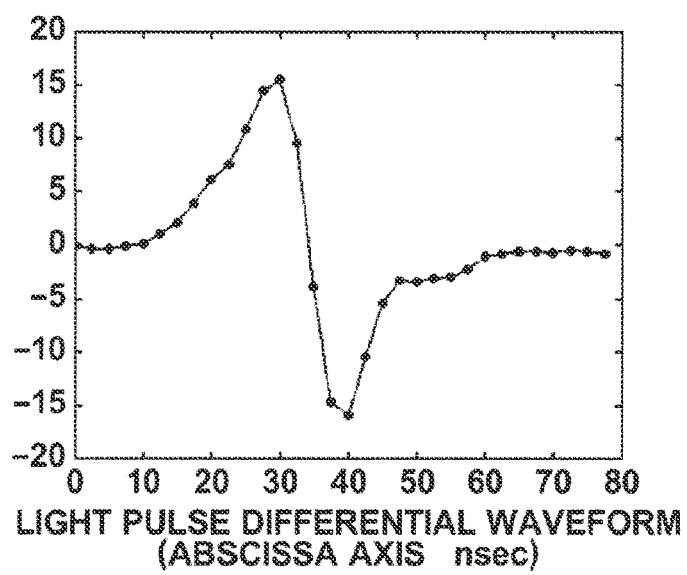
FIG. 2C is a waveform chart showing a light pulse differential waveform (h)
Figure 2D:
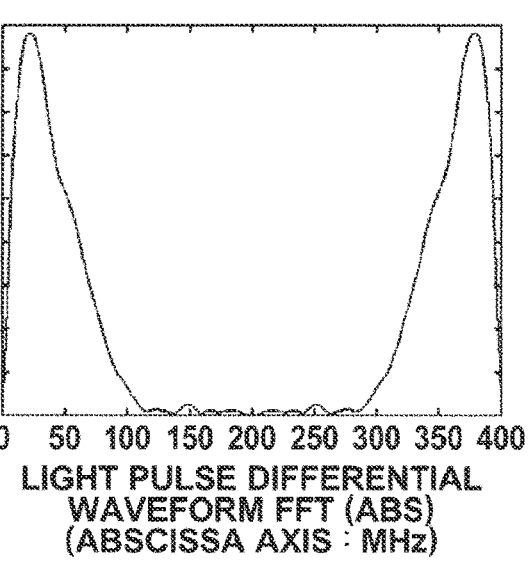
FIG. 2D is a waveform chart showing a light pulse differential waveform FFT (fft_h) after FFT.

A light pulse differential waveform h is subjected to a Fourier transform using FFT (step S102). FIG. 2C shows a light pulse differential waveform (h), and FIG. 2D shows the light pulse differential waveform FFT (fft_h) after FFT. By applying the Fourier transform to the time domain signal (waveform), as shown in FIG. 2C, the time domain signal is converted into the frequency domain signal, as shown in FIG. 2D. It should be noted that the black circles shown in FIG. 20 represent sampling points of the light pulse differential waveform. Although FIG. 2D shows absolute values of the light pulse differential waveform FFT, complex numbers are handled in the actual processing.

Figure 2E:
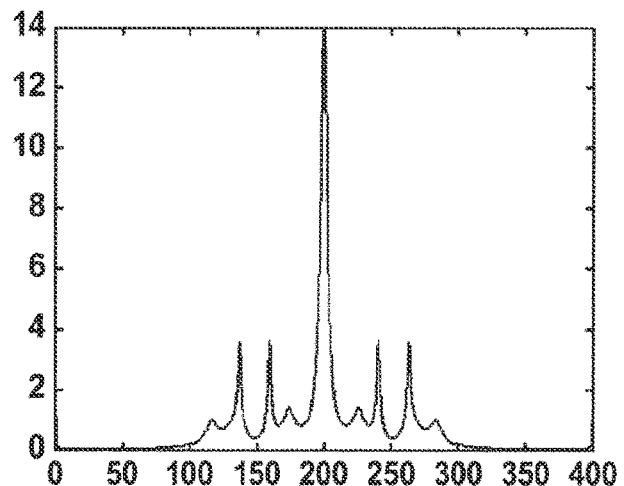
FIG. 2E is a waveform chart showing a light pulse differential waveform FFT filter.

As a light pulse differential waveform FFT filter (inverse filter), a reciprocal of the light pulse differential waveform FFT(fft_h) after FFT, which is obtained in step S102, is calculated (step S103). Specifically, the light pulse differential waveform FFT filter can be calculated by:

$$\text{conj}(fft\_h)/abs(fft\_h)^2,$$

where conj(fft_h) represents a conjugate complex number of fft_h, and abs(fft_h) represents an absolute value of fft_h. FIG. 2E shows the light pulse differential waveform FFT filter. By calculating the reciprocal of the light pulse differential waveform FFT shown in FIG. 2D, the light pulse differential waveform FFT filter as shown in FIG. 2E can be obtained.

Figure 2F:
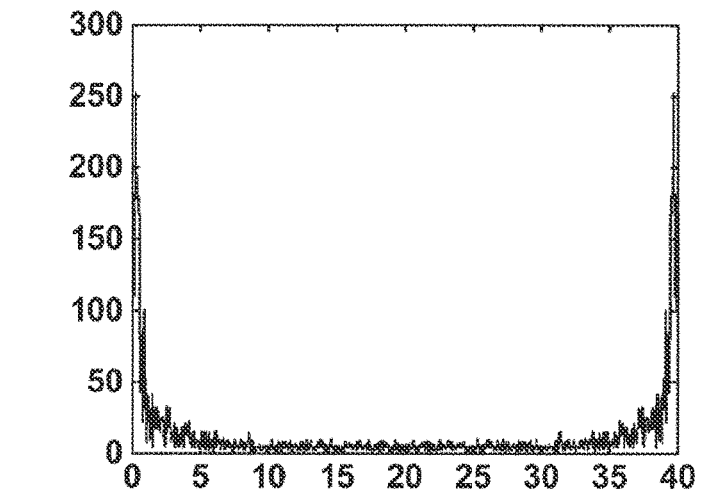
FIG. 2F is a waveform chart showing a FFT waveform after deconvolution.

For each element, the photoacoustic signal FFT is multiplied by the light pulse differential FFT filter obtained as described above to deconvolve the light pulse differential waveform from the photoacoustic signal FFT (step S104). FIG. 2F shows the FFT waveform after deconvolution. By multiplying the photoacoustic signal FFT shown in FIG. 2B by the light pulse differential waveform FFT filter shown in FIG. 2E, the FFT waveform shown in FIG. 2F is obtained.

Figure 2G:
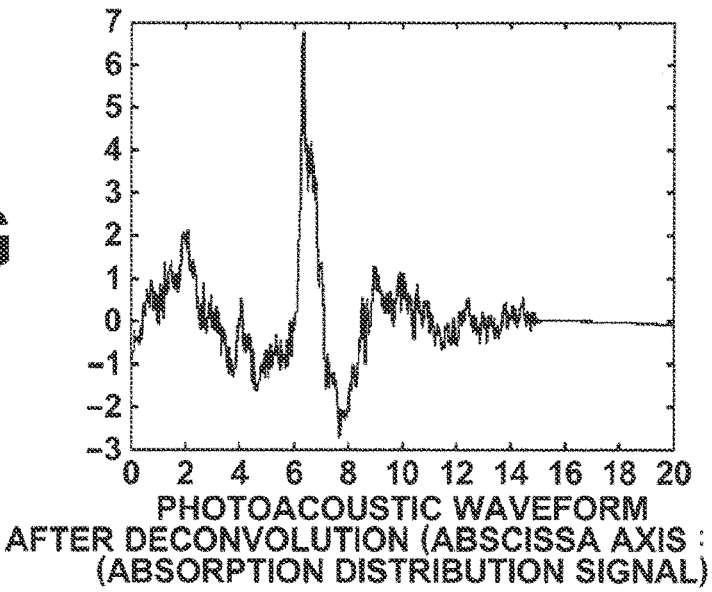
FIG. 2G is a waveform chart showing a photoacoustic signal after inverse transform.

The FFT waveform from which the light pulse differential waveform has been deconvolved in step S104 is then subjected to an inverse Fourier transform using inverse FFT to convert the frequency domain signal back into a time domain signal (step S105). FIG. 2G shows the photoacoustic signal after inverse transform. By applying the inverse FFT to the FFT waveform (frequency domain signal) shown in FIG. 2F, the photoacoustic signal after deconvolution (time domain signal) shown in FIG. 2G is obtained. This photoacoustic signal after deconvolution corresponds to the absorption distribution, which is obtained by deconvolving the light pulse differential waveform from the photoacoustic signal after reconstruction (FIG. 2A) representing the light absorption distribution with the light pulse differential waveform (FIG. 2C) convolved therein.

Figure 3A:
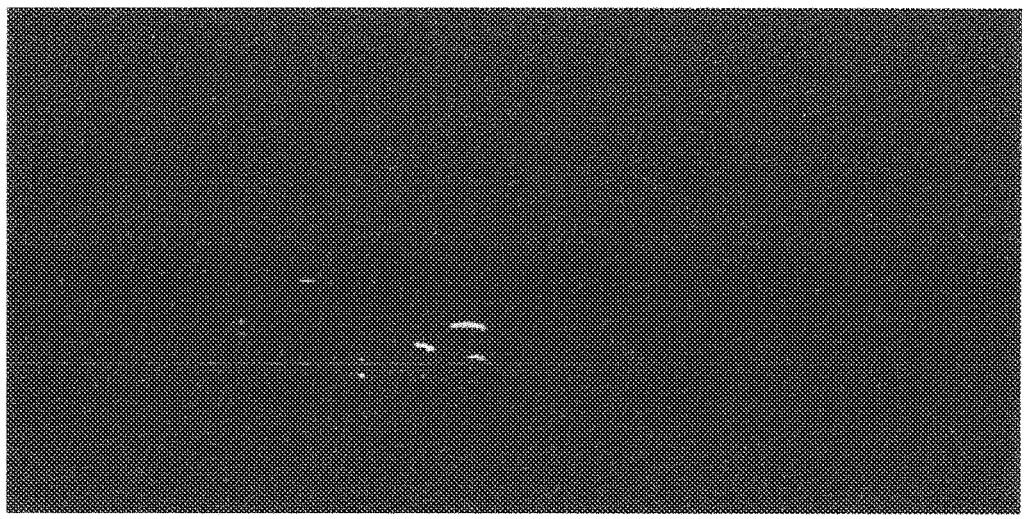
FIG. 3A shows a photoacoustic image generated based on a photoacoustic signal after reconstruction.
Figure 3B:
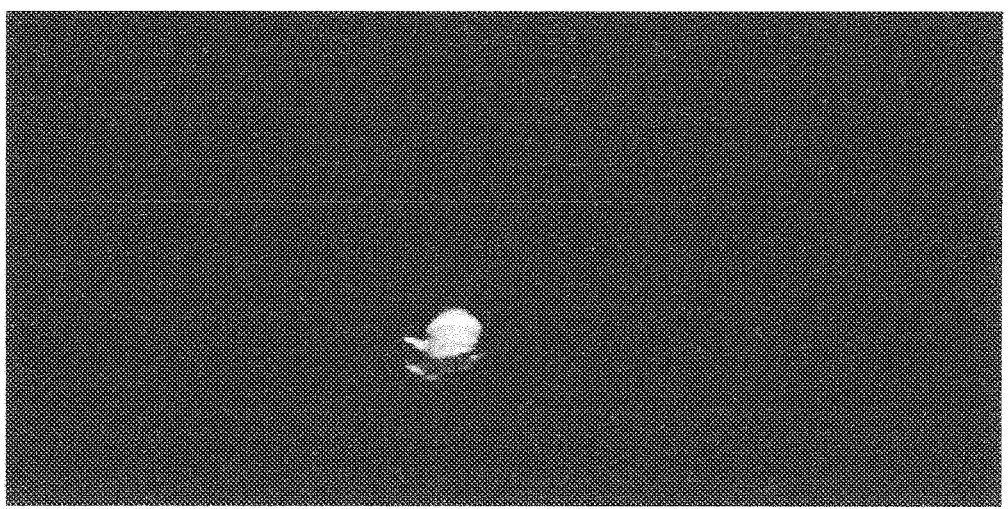
FIG. 3B shows a photoacoustic image generated based on a photoacoustic signal after deconvolution.

FIG. 3A shows a photoacoustic image that is generated based on the photoacoustic signal after reconstruction (FIG. 2A), and FIG. 3B shows a photoacoustic image that is generated based on the photoacoustic signal after deconvolution (FIG. 2G). The photoacoustic image shown in FIG. 3A that is generated based on the photoacoustic signal after reconstruction is substantially an image of a pressure distribution, in which one blood vessel is shown doubled and it is difficult to confirm the position of each blood vessel during image interpretation. In contrast, the photoacoustic image shown in FIG. 3B that is generated based on the photoacoustic signal after deconvolution, from which the light pulse differential waveform has been deconvolved, is an image of distribution of absorptive substances, and it is easier to confirm the position of each blood vessel.

Figure 4:
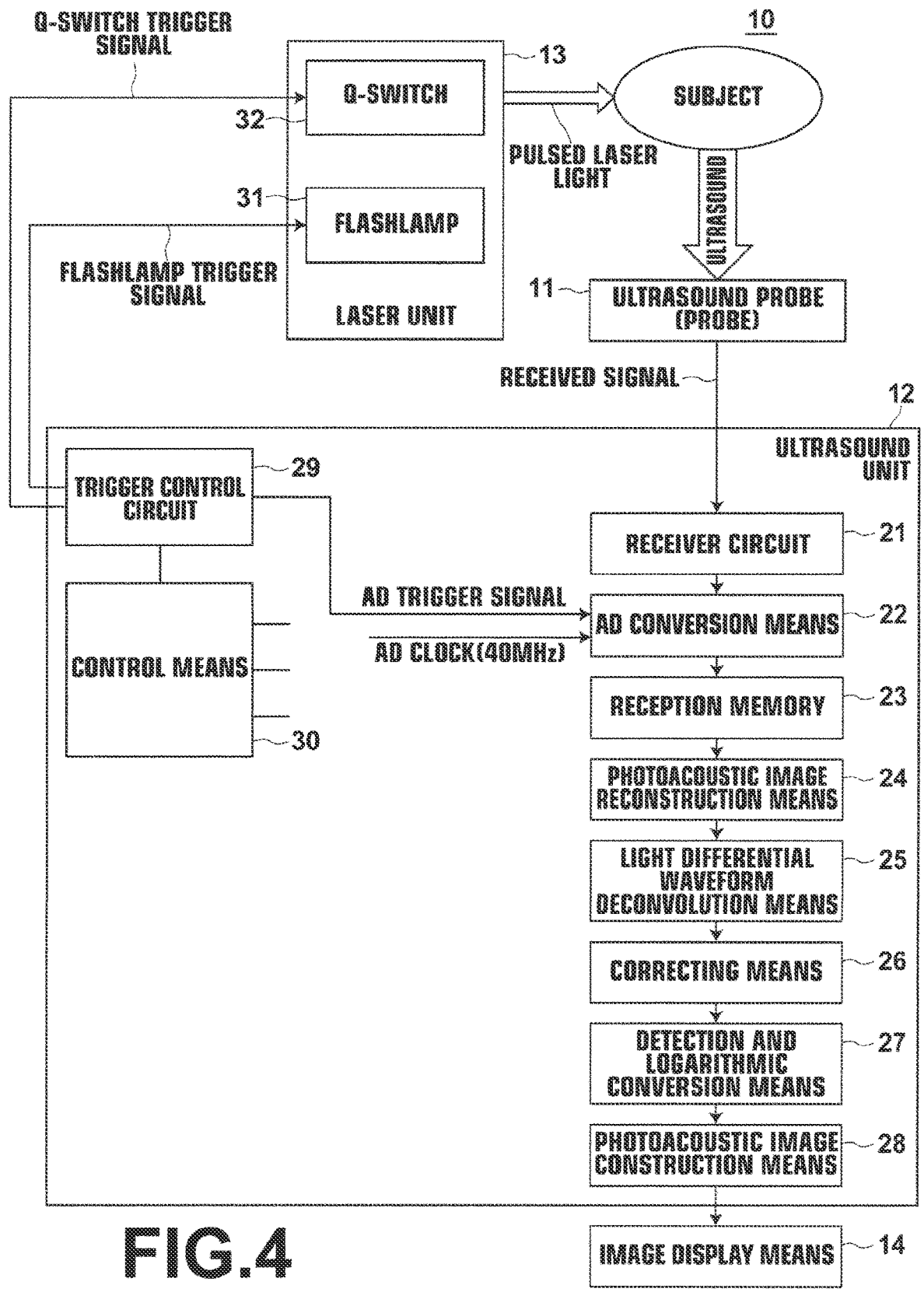
FIG. 4 is a block diagram illustrating a photoacoustic image generation apparatus including a photoacoustic signal processing device of a first embodiment of the invention.

Now, embodiments of the present invention are described in detail with reference to the drawings. FIG. 4 shows a photoacoustic image generation apparatus including a photoacoustic signal processing device of a first embodiment of the invention. The photoacoustic image generation apparatus (photoacoustic diagnostic imaging apparatus) 10 includes an ultrasound probe (probe) 11, an ultrasound unit 12 and a light source unit (laser unit) 13.

The laser unit 13 generates laser light to be applied to the subject. The wavelength of the laser light may be set appropriately depending on the object to be observed. The laser light outputted from the laser unit 13 is guided to the probe 11 with a light guide means, such as an optical fiber, and is applied to the subject from the probe 11. After the light outputted from the laser unit 13 is applied to the subject, the probe 11 detects ultrasound (a photoacoustic signal) that is generated when the laser light is absorbed by light-absorbing substances in the subject. The probe 11 includes a plurality of ultrasound transducers, which are arranged one-dimensionally, for example.

The ultrasound unit 12 corresponds to the photoacoustic signal processing device. The ultrasound unit 12 includes a receiver circuit 21, an AD conversion means 22, a reception memory 23, a photoacoustic image reconstruction means 24, a light differential waveform deconvolution means 25, a correcting means 26, a detection and logarithmic conversion means 27, a photoacoustic image construction means 28, a trigger control circuit 29 and a control means 30. The receiver circuit 21 receives the photoacoustic signal detected with the probe 11. The AD conversion means 22 is a sampling means, which samples the photoacoustic signal received by the receiver circuit 21 and converts the photoacoustic signal into a digital signal. AD conversion means 22 samples the photoacoustic signal at a predetermined sampling cycle based on an AD clock signal of a predetermined frequency, which is inputted externally, for example. The reception memory 23 stores the photoacoustic signal sampled by the AD conversion means 22.

The photoacoustic image reconstruction means 24 reads out the photoacoustic signal from the reception memory 23, and generates data of each line of the photoacoustic image based on the photoacoustic signal detected with the ultrasound transducers of the probe 11. The photoacoustic image reconstruction means 24 generates the data of each line by summing data from 64 ultrasound transducers, for example, of the probe 11 with a delay time depending on the position of each ultrasound transducer (a delay-and-sum method). In place of the delay-and-sum method, the photoacoustic image reconstruction means 24 may use a BP (Back Projection) method to perform the reconstruction. Still alternatively, the photoacoustic image reconstruction means 24 may use a Hough transform method or a Fourier transform method to perform the reconstruction.

The light differential waveform deconvolution means 25 generates, from the reconstructed photoacoustic signal, a signal from which the light pulse differential waveform (light differential waveform), which is a differential waveform of a temporal waveform of light intensity of the light applied to the subject, is deconvolved. By deconvolving the light pulse differential waveform, the reconstructed pressure distribution at $t=0$, i.e., the absorption distribution, can be obtained from a reconstructed pressure distribution at $t \neq 0$. The light differential waveform deconvolution means 25 may perform the deconvolution on a photoacoustic signal before reconstruction.

The correcting means 26 corrects the signal from which the light pulse differential waveform has been deconvolved to remove influence of reception angle-dependent properties of the ultrasound transducers of the probe 11 from the signal from which the light pulse differential waveform has been deconvolved. In addition to or in place of the reception angle-dependent properties, the correcting means 26 removes influence of an incoming light distribution on the subject from the signal from which the light pulse differential waveform has been deconvolved. The correcting means 26 may be omitted and a photoacoustic image may be generated without performing these corrections.

The detection and logarithmic conversion means 27 finds an envelope of data of each line after correction and applies logarithmic conversion to the found envelope. As a detection means to find the envelope, a conventionally used method, such as a Hilbert transform or quadrature detection, may be used. With this, influence of the band due to the natural vibration of the ultrasound transducers can be removed. The photoacoustic image construction means 28 generates a photoacoustic image based on the data of each line after logarithmic conversion. The photoacoustic image construction means 28 generates the photoacoustic image by, for example, converting positions in the time axis direction of the photoacoustic signal (peak portions) into positions in the depth direction of the photoacoustic image.

The control means 30 controls the individual components of the ultrasound unit 12. The trigger control circuit 29 sends a flashlamp trigger signal to the laser unit 13 when a photoacoustic image is generated. Also, the trigger control circuit 29 sends a Q-switch trigger signal after the flashlamp trigger signal is outputted. The laser unit 13 includes a flashlamp 31 and a Q-switch 32. In response to the flashlamp trigger signal, the laser unit 13 turns the flashlamp 31 on and starts laser excitation. When the Q-switch trigger signal is inputted, the laser unit 13 turns the Q-switch on to output pulsed laser light. The trigger control circuit 29 sends a sampling trigger signal to the AD conversion means 22 synchronously with application of the laser light to the subject, thereby controlling timing to start sampling of the photoacoustic signal by the AD conversion means 22.

Figure 5:
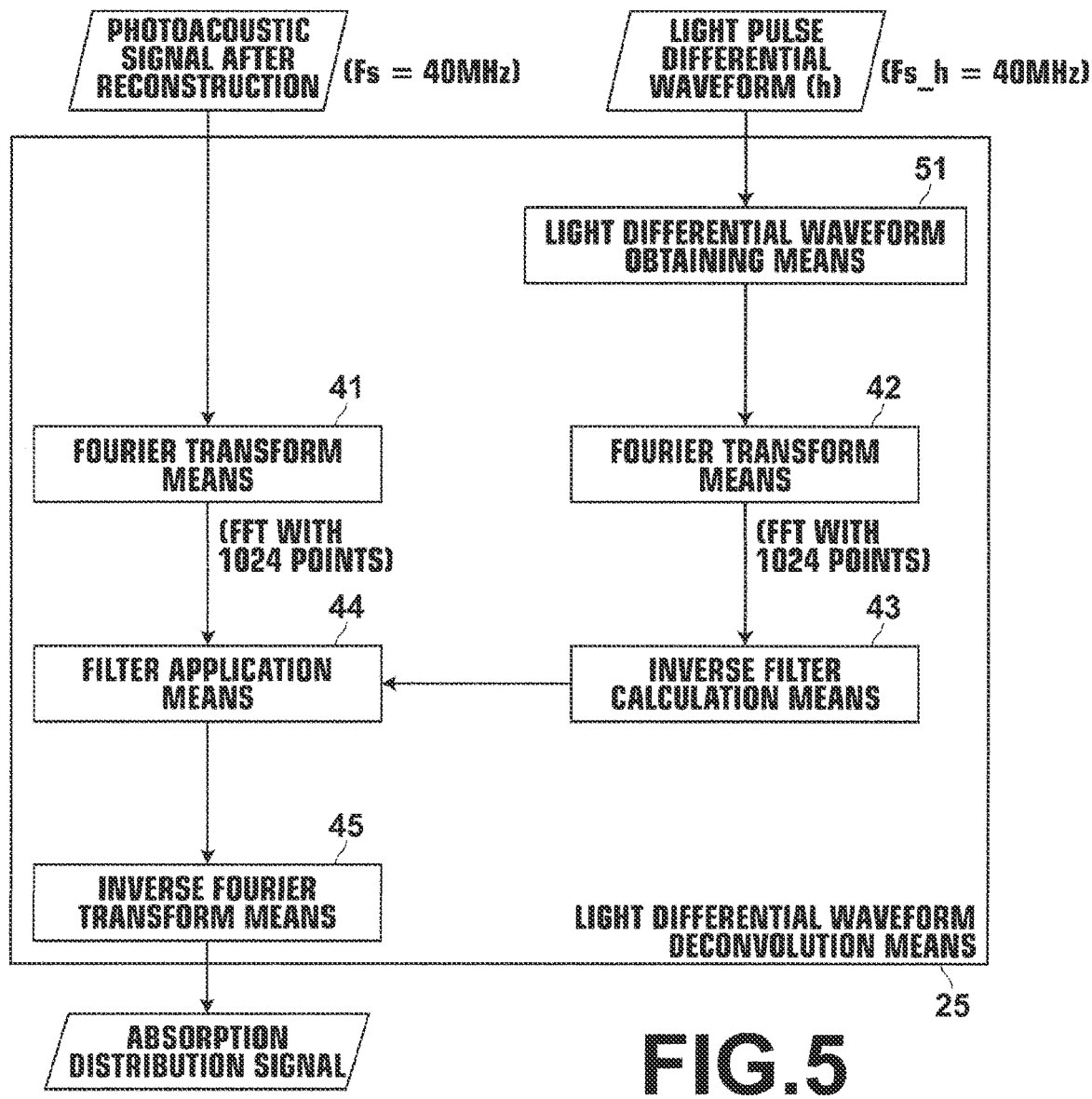
FIG. 5 is a block diagram illustrating a light differential waveform deconvolution means.

FIG. 5 shows the light differential waveform deconvolution means 25. The light differential waveform deconvolution means 25 includes Fourier transform means 41 and 42, an inverse filter calculation means 43, a filter application means 44, an inverse Fourier transform means 45 and a light differential waveform obtaining means 51. The light differential waveform obtaining means 51 obtains the light pulse differential waveform. The light differential waveform obtaining means 51 reads out the light pulse differential waveform from a memory, for example. Alternatively, the light differential waveform obtaining means 51 may read out a temporal waveform of light intensity of the light applied to the subject from a memory and may differentiate the temporal waveform with respect to time. Still alternatively, the light differential waveform obtaining means 51 may obtain the light pulse differential waveform by measuring the temporal waveform of light intensity of the light applied to the subject and differentiating the result of the measurement with respect to time. Yet alternatively, the light differential waveform obtaining means 51 may obtain the light pulse differential waveform by using a function that represents the temporal waveform of light intensity of the pulsed light applied to the subject or a differential waveform thereof, where a pulse duration of the pulsed light is an independent variable, and a result of measurement of the pulse duration of the pulsed light applied to the subject.

The Fourier transform means (first Fourier transform means) 41 converts the reconstructed photoacoustic signal from the time domain signal to a frequency domain signal using a discrete Fourier transform. The Fourier transform means (second Fourier transform means) 42 converts a signal obtained by sampling the light pulse differential waveform at a predetermined sampling rate from the time domain signal to a frequency domain signal using a discrete Fourier transform. As an algorithm for the Fourier transform, FFT can be used.

In this embodiment, it is assumed that the sampling rate of the photoacoustic signal is the same as the sampling rate of the light pulse differential waveform. For example, the photoacoustic signal is sampled synchronously with a sampling clock of Fs=40 MHz, and the light differential pulse is also sampled at a sampling rate of Fs_h=40 MHz. The Fourier transform means 41 applies a Fourier transform of 1024 points, for example, to the photoacoustic signal sampled at 40 MHz. Also, the Fourier transform means 42 applies a Fourier transform of 1024 points to the light pulse differential waveform sampled at 40 MHz.

The inverse filter calculation means 43 calculates, as the inverse filter, a reciprocal of the Fourier-transformed light pulse differential waveform. For example, the inverse filter calculation means 43 calculates conj (fft_h)/abs (fft_h)$^2$, where fft_h is the signal obtained by applying the Fourier transform to the light pulse differential waveform h, as the inverse filter. The filter application means 44 applies the inverse filter calculated by the inverse filter calculation means 43 to the Fourier transformed photoacoustic signal provided by the Fourier transform means 41. For example, the filter application means 44 multiplies, for each element, the Fourier coefficient of the photoacoustic signal by the Fourier coefficient of the inverse filter. By applying the inverse filter, the light pulse differential waveform is deconvolved from the frequency domain signal. The inverse Fourier transform means 45 converts the photoacoustic signal processed with the inverse filter from the frequency domain signal to a time domain signal using an inverse Fourier transform. By applying the inverse Fourier transform, a time domain absorption distribution signal is obtained.

Figure 6:
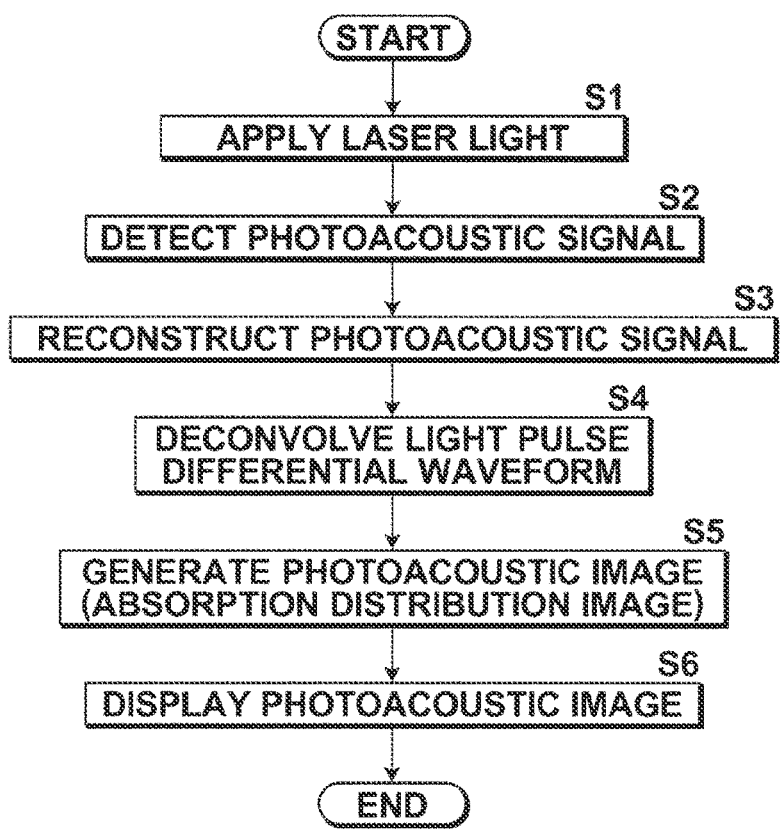
FIG. 6 is a flow chart illustrating the procedure of operation to generate a photoacoustic image.

FIG. 6 shows a procedure of operation. The trigger control circuit 29 outputs a flashlamp trigger signal to the laser unit 13. In response to the flashlamp trigger signal, the laser unit 13 turns the flashlamp 31 on. The trigger control circuit 29 outputs a Q-switch trigger signal at predetermined timing. When the Q-switch trigger signal is inputted, the laser unit 13 turns the Q-switch 32 on to output pulsed laser light. The outputted pulsed laser light is guided to the probe 11, for example, and is applied to the subject from the probe 11 (step S1).

After the laser light is applied to the subject, the probe 11 detects a photoacoustic signal generated in the subject due to the application of the laser light (step S2). The receiver circuit 21 of the ultrasound unit 12 receives the photoacoustic signal detected with the probe 11. The trigger control circuit 29 sends a sampling trigger signal to the AD conversion means 22 in time with the application of the light to the subject. In response to the sampling trigger signal, the AD conversion means 22 starts sampling of the photoacoustic signal and stores the sampled data of the photoacoustic signal in the reception memory 23.

The photoacoustic image reconstruction means 24 reads out the sampled data of the photoacoustic signal from the reception memory 23, and reconstructs a photoacoustic signal based on the read-out sampled data of the photoacoustic signal (step S3). The light differential waveform deconvolution means 25 deconvolves the light pulse differential waveform, which is obtained by differentiating the temporal waveform of light intensity of the pulsed laser light applied to the subject, from the reconstructed photoacoustic signal (step S4). With this deconvolution, a photoacoustic signal showing the absorption distribution is obtained.

The correcting means 26 corrects the signal from which the light pulse differential waveform has been deconvolved for the reception angle dependence of the detector element and the incoming light distribution on the subject. The detection and logarithmic conversion means 27 finds an envelope of the photoacoustic signal corrected by the correcting means 26, and applies logarithmic conversion to the found envelope. The photoacoustic image construction means 28 generates a photoacoustic image based on data of each line after logarithmic conversion (step S5). This photoacoustic signal is an absorption distribution image imaging the absorption distribution. The image display means 14 displays the photoacoustic image, which is the absorption distribution image, on a display screen (step S6).

In this embodiment, the photoacoustic image reconstruction means 24 once reconstructs a photoacoustic signal (photoacoustic image) as a pressure distribution at the light emission clock time (t=0) using a usual reconstruction method. Then, since the actual light emission time has a finite length, the clock time, which is assumed to be t=0 for the reconstruction, is regarded as a time having a finite length, and the light differential waveform deconvolution means 25 deconvolves the light pulse differential waveform from the reconstructed photoacoustic image. By deconvolving the light pulse differential waveform, the absorption distribution can be obtained and an absorption distribution image can be generated. By employing the above-described technique, imaging of the absorption distribution can be achieved with a practical light pulse duration and a practical ultrasound system or when an actual living body is observed. This is advantageous in that the band and AD sampling of a detector of a current system can be used. Further, in this embodiment, a pressure distribution is once outputted during reconstruction of a photoacoustic image, and this is highly compatible with existing ultrasound algorithms and devices.

In comparison with Non-Patent Document 2, the deconvolution in Non-Patent Document 2 is performed in a state where the light differential function and the device impulse response function are inseparable. In a case where a usual narrow-band ultrasound probe, such as an 8-MHz ultrasound probe, is used, a signal of 4 to 12 MHz can be detected with the ultrasound probe. However, since the sensitivity at 4 MHz and 12 MHz, which are ends of the band, is low, S/N at 4 MHz and 12 MHz is lower than S/N at 8 MHz. In Non-Patent Document 2, it is emphasized to take (correct) the device impulse response into account. Therefore, signals at 4 MHz and 12 MHz where the sensitivity is low are emphasized, resulting in an image with frequency components having poor S/N being emphasized. In contrast, in the present invention, only the light pulse differential waveform is deconvolved. In this case, components corresponding to the device impulse response can be removed after the deconvolution while processing without lowering the S/N with the light pulse differential waveform, thereby allowing generation of a photoacoustic image without lowering the S/N.

Next, a second embodiment of the invention is described. In the first embodiment, the sampling rate of the photoacoustic signal is the same as the sampling rate of the light pulse differential waveform, and the both signals are subjected to the Fourier transform of the same number of data points. In this embodiment, the photoacoustic signal is obtained by low-speed sampling, and the light pulse differential waveform is obtained by high-speed sampling. That is, the sampling rate of the light pulse differential waveform is set higher than the sampling rate of the photoacoustic signal. For example, a sampling interval (the reciprocal of the sampling rate) of the photoacoustic signal is set longer than the pulse duration of the light applied to the subject. When the Fourier transform is performed, the photoacoustic signal sampled at a low sampling rate is resampled (upsampled) at the same sampling rate as the sampling rate of the light pulse differential waveform prior to the Fourier transform. Other points may be the same as those of the first embodiment.

Figure 7:
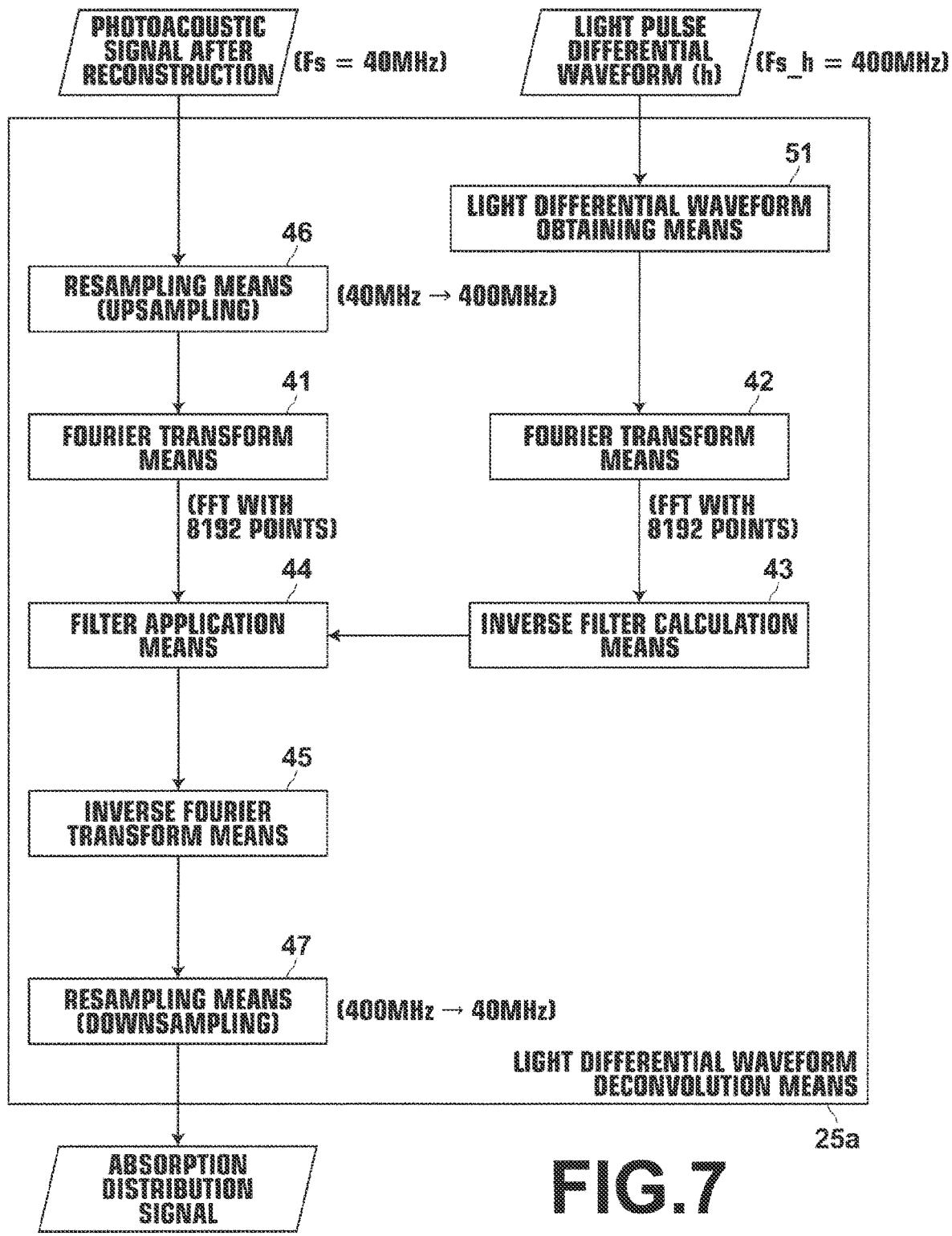
FIG. 7 is a block diagram illustrating a light differential waveform deconvolution means of a second embodiment of the invention.

FIG. 7 shows a light differential waveform deconvolution means 25a of this embodiment. The light differential waveform deconvolution means 25a of this embodiment includes resampling means 46 and 47, in addition to the configuration of the light differential waveform deconvolution means 25 of the first embodiment shown in FIG. 5. The resampling means 46 is an upsampling means, and upsamples the sampled data of the photoacoustic signal, which has been sampled at a low sampling rate, at the same sampling rate as the sampling rate of the light pulse differential waveform. The resampling means 46 achieves the upsampling by, for example, adding zero between sample points of the photoacoustic signal sampled at a low sampling rate and applying a low-pass filter with a cut off frequency equal to a Nyquist frequency before the upsampling.

For example, it is assumed that the sampling rate (first sampling rate) of the photoacoustic signal at the AD conversion means 22 (FIG. 4) is 40 MHz and the sampling rate (second sampling rate) of the light pulse differential waveform is 400 MHz. In this case, the resampling means 46 upsamples the photoacoustic signal of 40 MHz into a signal of 400 MHz. The Fourier transform means 41 applies a Fourier transform to the photoacoustic signal upsampled by the resampling means 46. The Fourier transform means 41, which applies the Fourier transform to the photoacoustic signal, and the Fourier transform means 42, which applies the Fourier transform to the light pulse differential waveform, perform the Fourier transform of the same number of data points. For example, the Fourier transform means 41 converts the photoacoustic signal into a 8192-point frequency domain signal, and the Fourier transform means 42 converts the light pulse differential waveform into a 8192-point frequency domain signal.

The filter application means 44 applies the inverse filter to the signal obtained by applying the Fourier transform to the upsampled photoacoustic signal. The inverse Fourier transform means 45 converts the signal processed with the inverse filter from the frequency domain signal into a time domain signal (absorption distribution). The absorption distribution signal converted back into the time domain signal is, for example, an upsampled signal of 400 MHz. The resampling means 47 downsamples the absorption signal such that the absorption distribution signal becomes a signal sampled at the original sampling rate of the photoacoustic signal. For example, the resampling means 47 downsamples the absorption signal of 400 MHz into an absorption signal of 40 MHz. The downsampling is achieved, for example, by applying a low-pass filter with a cut off frequency equal to a Nyquist frequency after the downsampling and then decimating the sample points.

Figure 8A:
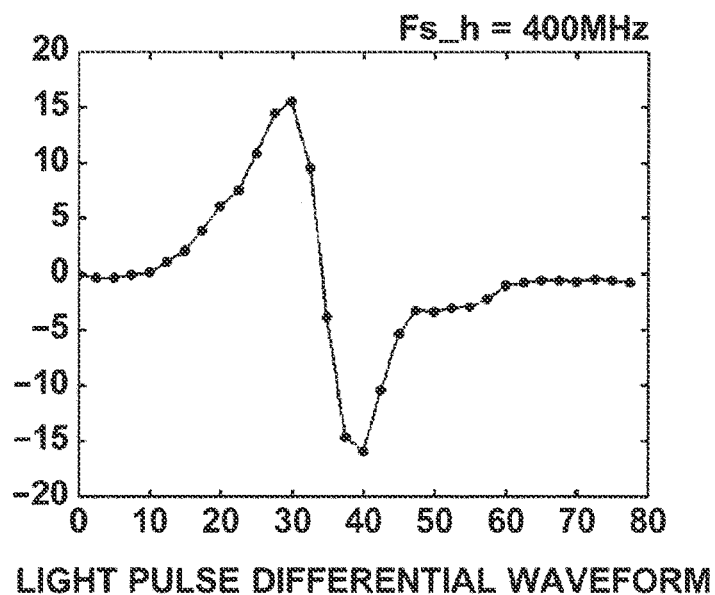
FIG. 8A is a waveform chart showing a light pulse differential waveform sampled at a sampling rate of 400 MHz.
Figure 8B:
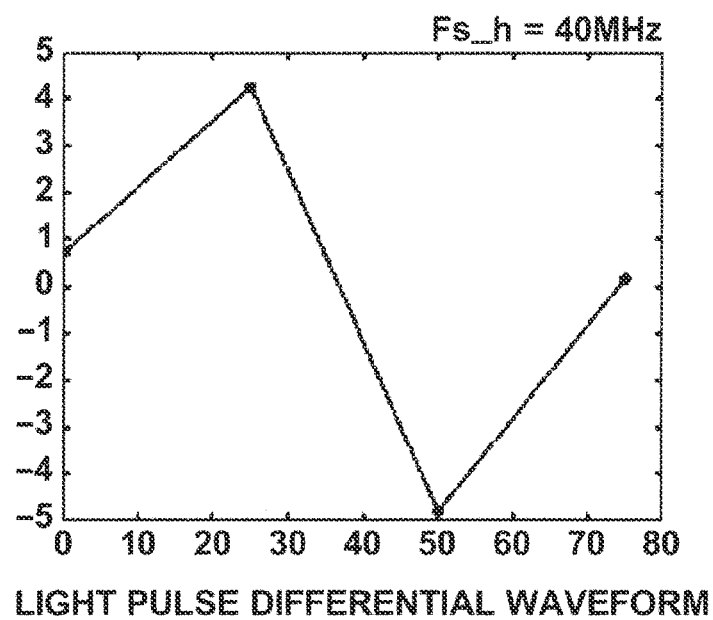
FIG. 8B is a waveform chart showing a light pulse differential waveform sampled at a sampling rate of 40 MHz.

FIG. 8A shows a light pulse differential waveform sampled at a sampling rate of 400 MHz, and FIG. 8B shows a light pulse differential waveform sampled at a sampling rate of 40 MHz. With the sampling rate of 400 MHz, the light pulse differential waveform can be accurately reproduced, as shown in FIG. 8A. On the other hand, when the light pulse differential waveform is sampled at the same sampling rate of 40 MHz as the sampling rate of the photoacoustic signal, the light pulse differential waveform cannot be reproduced accurately, as shown in FIG. 8B.

When the filter application means 44 applies the inverse filter to the signal obtained by applying the Fourier transform to the photoacoustic signal, it is necessary that the number of data points is the same. If the sampling rate of the light pulse differential waveform is set to be equal to the sampling rate of the photoacoustic signal, the sampling frequency is excessively low relative to the waveform change, and the light pulse differential waveform cannot be reproduced accurately, as shown in FIG. 8B. Then, if an inverse filter obtained from such a light pulse differential waveform is applied, accurate deconvolution of the light pulse differential term may not be achieved and it may be impossible to obtain a correct absorption distribution.

On the other hand, in a case where the sampling rate of the light pulse differential waveform is set at 400 MHz, for example, in order to accurately reproduce the light pulse differential waveform, and the sampling rate of the photoacoustic signal is also set at 400 MHz, accurate deconvolution of the light pulse differential term is achieved and a correct absorption distribution can be obtained. In this case, however, the AD conversion means 22 requires a high-speed AD converter, and the total number of the sampled data increases, which in turn increases the memory capacity required for the reception memory 23 (FIG. 4). Further, data handled by the photoacoustic image reconstruction means 24 increases and a longer time is taken for the reconstruction.

In this embodiment, the resampling means 46 resamples the sampled data of the photoacoustic signal. In this embodiment, the detected photoacoustic signal is upsampled during signal processing. Therefore, accurate deconvolution of the light pulse differential term can be achieved while using low speed sampling for the detection and the reconstruction of the photoacoustic signal. In this embodiment, the AD conversion means 22 does not require a high speed AD converter, and the memory capacity required for the reception memory 23 is not increased. Also, the time taken for the reconstruction of the photoacoustic signal is not increased, and the processing time can be reduced when compared to the case where the photoacoustic signal is sampled at a high sampling rate during the detection thereof.

Next, a third embodiment of the invention is described. In this embodiment, similarly to the second embodiment, the sampling rate of the light pulse differential waveform is set higher than the sampling rate of the photoacoustic signal. In the second embodiment, the photoacoustic signal sampled at a low sampling rate is upsampled, and both the signals are subjected to the Fourier transform of the same number of data points. In this embodiment, the number of data points of the Fourier transform applied to the light pulse differential waveform is higher than the number of data points of the Fourier transform applied to the photoacoustic signal, and zero points of a number corresponding to the difference between the numbers of data points are added at the center (a high frequency component region) of the Fourier transformed photoacoustic signal. Other points may be the same as those of the first embodiment.

Figure 9:
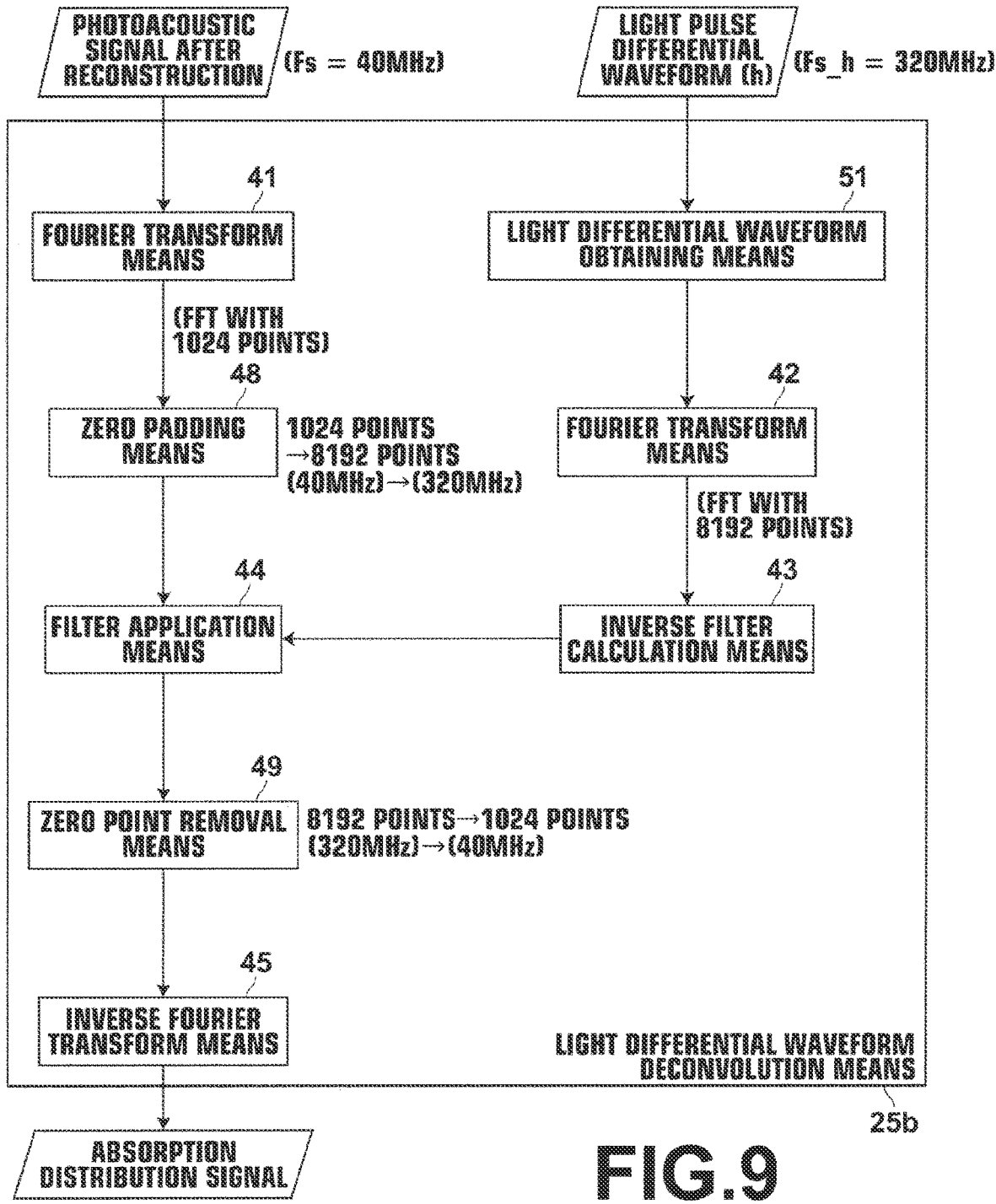
FIG. 9 is a block diagram illustrating a light differential waveform deconvolution means of a third embodiment of the invention.

FIG. 9 shows a light differential waveform deconvolution means 25b of this embodiment. The light differential waveform deconvolution means 25b of this embodiment includes a zero padding means 48 and a zero point removal means 49, in addition to the configuration of the light differential waveform deconvolution means 25 of the first embodiment shown in FIG. 5. It is assumed, for example, that the sampling rate of the photoacoustic signal (first sampling rate) is 40 MHz and the sampling rate of the light pulse differential waveform (second sampling rate) is 320 MHz. For example, the Fourier transform means 41 converts the photoacoustic signal of 40 MHz into a 1024-point (which is a first number of data points) frequency domain signal, and the Fourier transform means 42 converts the light pulse differential waveform of 320 MHz into a 8192-point (which is a second number of data points) frequency domain signal. The second number of data points is equal to or greater than a number of data points that is obtained by multiplying the first number of data points by a ratio of the second sampling rate to the first sampling rate.

The photoacoustic signal converted into the frequency domain signal is inputted from the Fourier transform means 41 to the zero padding means 48. The zero padding means 48 adds zero points (points with a signal value of zero) of a number corresponding to a difference between the numbers of data points of the Fourier transformed photoacoustic signal and of the light pulse differential waveform at the center of the Fourier transformed photoacoustic signal. For example, the zero padding means 48 divides a photoacoustic signal (frequency domain) with 1024 data points into two at the central frequency of the frequency band, and adds, between the divided two frequency domains, zero points of a number corresponding to a difference of the number of data points to generate a photoacoustic signal with 8192 data points, which is the same number of data points as that of the light pulse differential waveform (frequency domain). The addition of zero points is equivalent to upsampling in the frequency domain.

The filter application means 44 applies the inverse filter to the zero-padded signal provided by the zero padding means 48. The zero point removal means 49 removes a frequency band with "0" added by the zero padding means 48 from the signal processed with the inverse filter. For example, in a case where the zero padding means 48 has converted a photoacoustic signal (frequency domain) with 1024 data points into a signal with 8192 data points, the zero point removal means 49 converts the signal (with 8192 data points) processed with the filter back into a signal with 1024 data points. The removal of zero points is equivalent to downsampling in the frequency domain. The inverse Fourier transform means 45 converts the thus converted signal with 1024 data points from the frequency domain signal to a time domain signal.

Figure 10A:
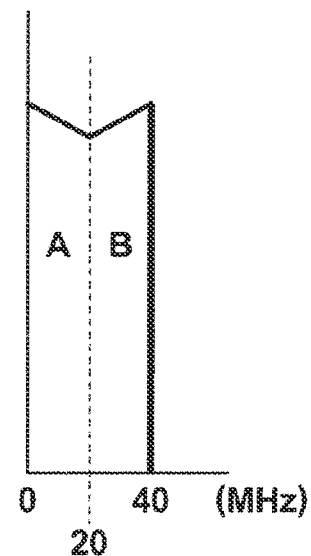
FIG. 10A is a graph showing a photoacoustic signal (frequency domain)
Figure 10B:
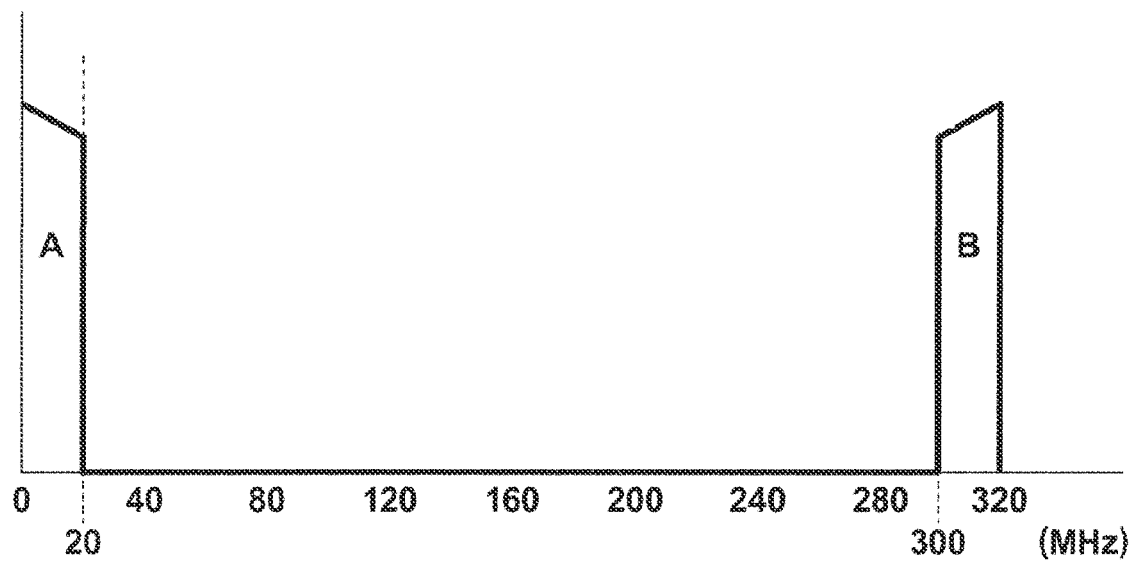
FIG. 10B is a graph showing a photoacoustic signal after zero padding.

FIG. 10A shows a Fourier transformed photoacoustic signal, and FIG. 10B shows a photoacoustic signal after zero padding. For example, in a case where the sampling rate of the photoacoustic signal at the AD conversion means 22 (FIG. 4) is 40 MHz, a signal obtained by applying the Fourier transform to the photoacoustic signal is a signal with a frequency band from 0 MHz to 40 MHz, as shown in FIG. 10A. This signal is divided into two regions A and B at 20 MHz, which is the Nyquist frequency (½ of the sampling frequency). The zero padding means 48 inserts 7168 zero points (8192−1024=7168) between the two regions, as shown in FIG. 10B. As a result of the addition of zero points, the signal of the region B becomes a signal corresponding to a frequency range from 300 MHz to 320 MHz.

In this embodiment, the photoacoustic signal sampled at a low sampling rate is converted into a frequency domain signal, and zero points are added to the high frequency component region of the converted frequency domain signal. The difference between this embodiment and the second embodiment lies in that, in the second embodiment, the photoacoustic signal (of the time domain) is upsampled; whereas, in this embodiment, the photoacoustic signal of the frequency domain is upsampled. In the case where the resampling (upsampling) is performed to fill a difference of the band between the signals in the frequency domain, in place of the time domain, accurate deconvolution of the light pulse differential term can be achieved while using low speed sampling for the detection and the reconstruction of the photoacoustic signal, similarly to the second embodiment.

Next, a fourth embodiment of the invention is described. In this embodiment, similarly to the second and third embodiments, the sampling rate of the light pulse differential waveform is set higher than the sampling rate of the photoacoustic signal. In this embodiment, the Fourier transform of the light pulse differential waveform is performed with the number of data points that is higher than the number of data points of the Fourier transform applied to the photoacoustic signal. Then, high frequency component sample points are removed from the Fourier transformed light differential waveform, and a reciprocal of the resulting light differential waveform is calculated as the inverse filter. Other points may be the same as those of the first embodiment.

Figure 11:
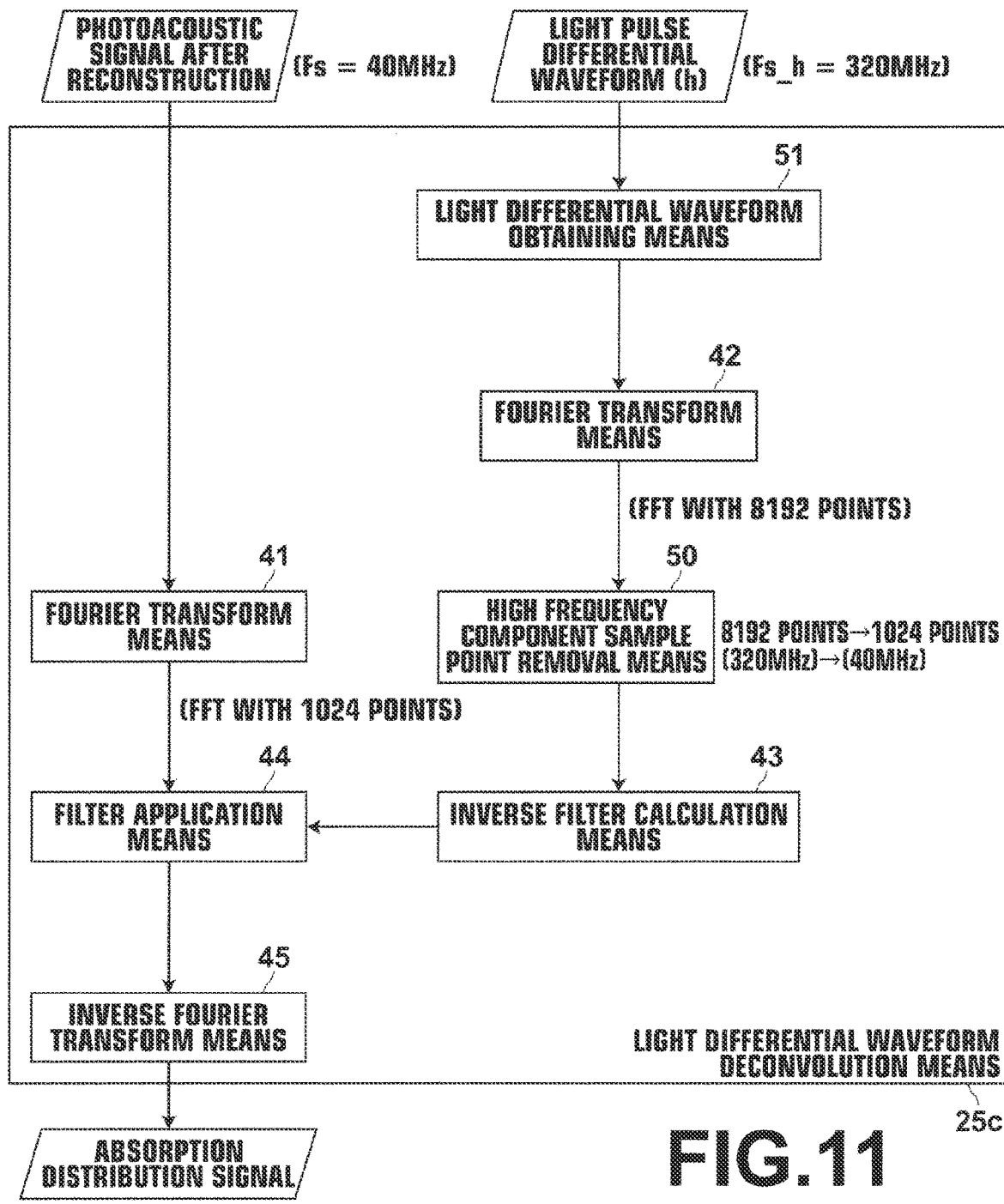
FIG. 11 is a block diagram illustrating a light differential waveform deconvolution means of a fourth embodiment of the invention.

FIG. 11 shows a light differential waveform deconvolution means 25c of this embodiment. The light differential waveform deconvolution means 25c of this embodiment includes a high frequency component sample point removal means 50, in addition to the configuration of the light differential waveform deconvolution means 25 of the first embodiment shown in FIG. 5. For example, it is assumed that the sampling rate of the photoacoustic signal (first sampling rate) is 40 MHz, and the sampling rate of the light pulse differential waveform (second sampling rate) is 320

MHz. For example, the Fourier transform means 41 converts the photoacoustic signal of 40 MHz into a 1024-point (which is a first number of data points) frequency domain signal, and the Fourier transform means 42 converts the light pulse differential waveform of 320 MHz into a 8192-point (which is a second number of data points) frequency domain signal. The second number of data points is equal to or greater than a number of data points that is obtained by multiplying the first number of data points by a ratio of the second sampling rate to the first sampling rate.

The light pulse differential waveform converted into the frequency domain signal is inputted from the Fourier transform means 42 to the high frequency component sample point removal means 50. The high frequency component sample point removal means 50 removes, from the Fourier transformed light pulse differential waveform, high frequency component sample points of a number corresponding to a difference between the numbers of data points of the Fourier transformed photoacoustic signal and of the light pulse differential waveform. For example, the high frequency component sample point removal means 50 deletes data points at the center corresponding to high frequency components from the light pulse differential waveform (frequency domain) with 8192 data points to generate a light pulse differential waveform with 1024 data points, which is the same number of data points as that of the photoacoustic signal (frequency domain). The removal of the high frequency component sample points is equivalent to downsampling of the light pulse differential waveform of the frequency domain.

Figure 12A:
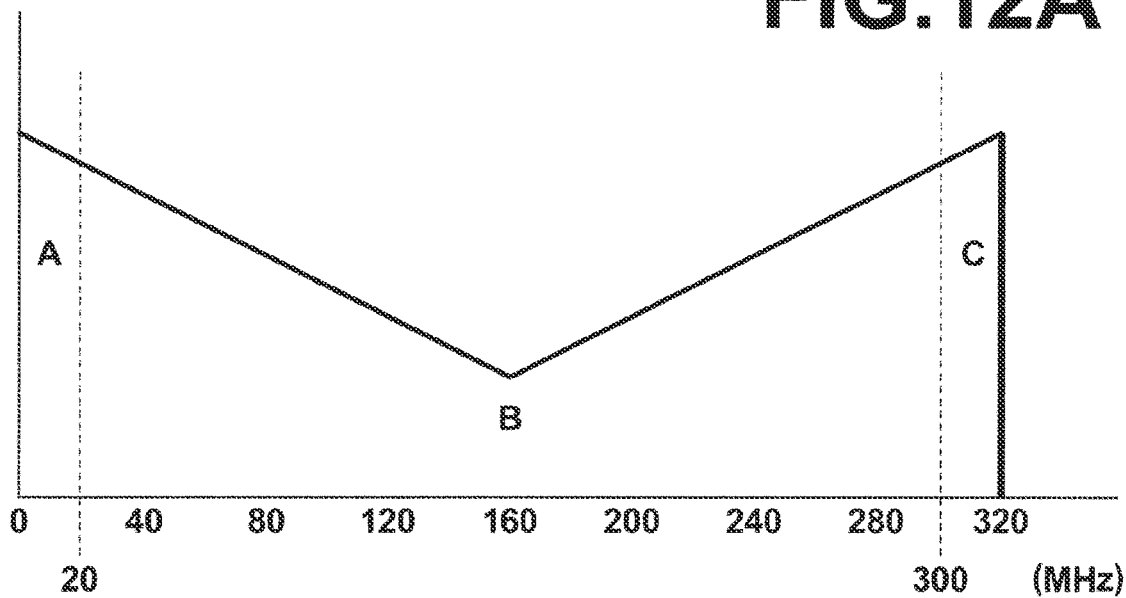
FIG. 12A is a graph showing a light pulse differential waveform (frequency domain)
Figure 12B:
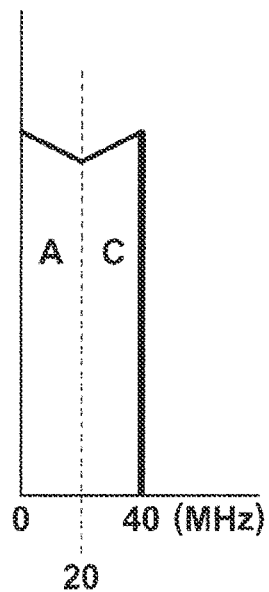
FIG. 12B is a graph showing a light pulse differential waveform after removal of high frequency component sample points.

FIG. 12A shows a Fourier transformed light pulse differential waveform, and FIG. 12B shows a light pulse differential waveform after removal of high frequency component sample points. For example, in the case where the sampling rate of the light pulse differential waveform is 320 MHz, the signal (with 8192 data points) obtained by applying the Fourier transform to the light pulse differential waveform is a signal with a frequency band from 0 MHz to 320 MHz, as shown in FIG. 12A. This signal is divided into three regions including a region from the 1st data point to the 512th data point (region A), a region from the 513th data point to the 7680th data point (region B) and a region from the 7681st data point to the 8192nd data point (region C), and the data points in the region B are removed. As shown in FIG. 12B, the region A and the region C are joined together to provide a light pulse differential waveform (frequency domain) with 1024 data points corresponding to the frequency band from 0 MHz to 40 MHz.

The inverse filter calculation means 43 calculates, as the inverse filter, a reciprocal of the light pulse differential waveform (frequency domain) after removal of high frequency component sample points. For example, the inverse filter calculation means 43 calculates, as the inverse filter, a reciprocal of the light pulse differential waveform with the number of data points reduced from 8192 to 1024. The filter application means 44 multiplies, for each element, the photoacoustic signal (frequency domain) with 1024 data points, for example, by the inverse filter. The inverse Fourier transform means 45 converts the signal processed with the inverse filter from the frequency domain signal to a time domain signal.

In the third embodiment, the filter application means 44 multiplies the photoacoustic signal (frequency domain) with zero points added to the high frequency component region shown in FIG. 10B by the reciprocal of the light pulse differential waveform (frequency domain) shown in FIG. 12A. Since the value of the high frequency component region of the photoacoustic signal is "0", the high frequency components (the region B shown in FIG. 12A) of the light pulse differential waveform does not influence the photoacoustic signal processed with the inverse filter. Therefore, the same result as the result in the third embodiment is obtained in this embodiment, where the high frequency component sample points are removed from the frequency domain signal of the light pulse differential waveform, the inverse filter is calculated from the light pulse differential waveform after removal of the high frequency component sample points, and the thus calculated inverse filter is applied to the photoacoustic signal (frequency domain). That is, the same effect as that of the third embodiment is obtained in this embodiment.

Figure 13:
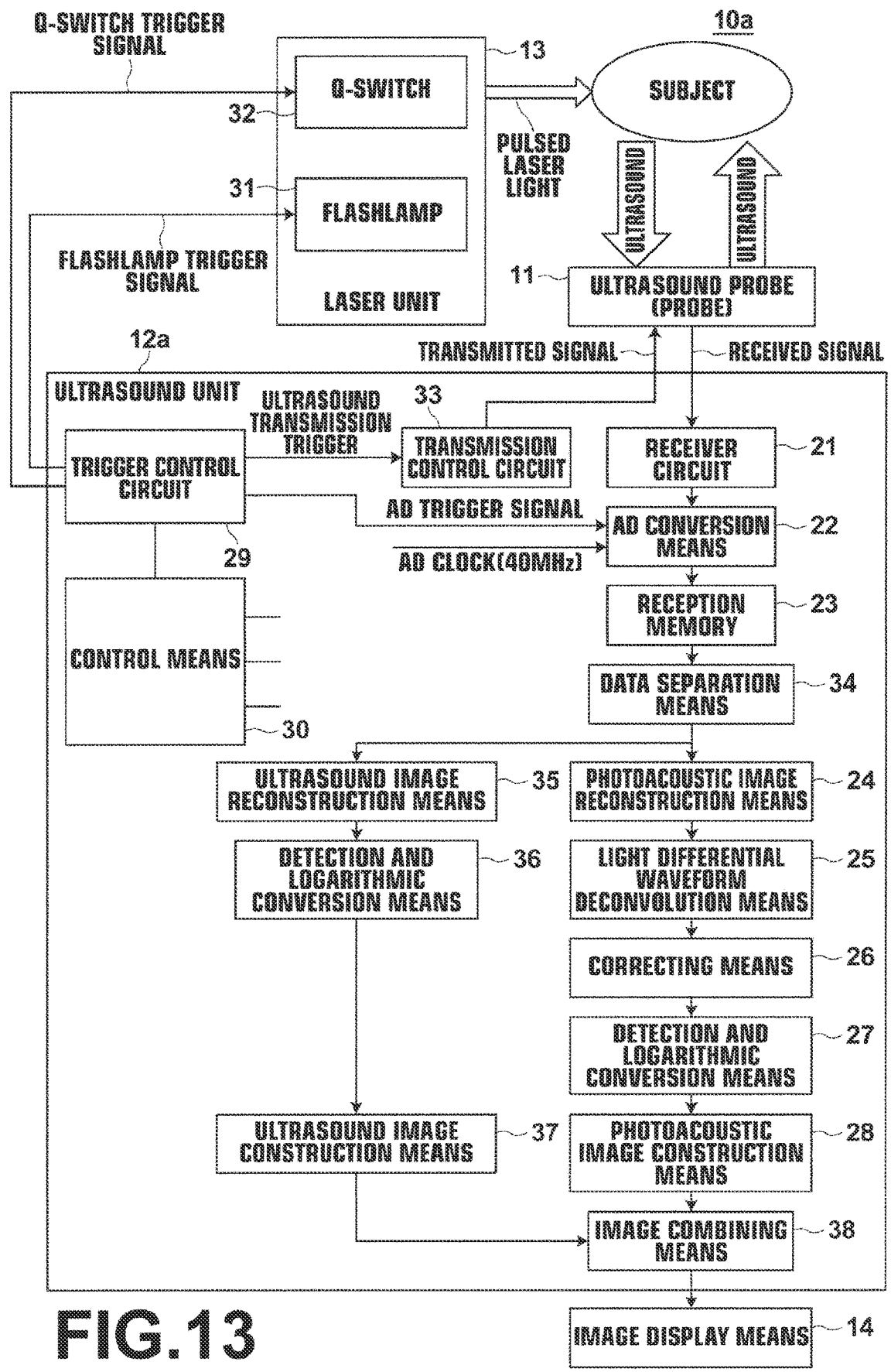
FIG. 13 is a block diagram illustrating a photoacoustic image generation apparatus of a fifth embodiment of the invention.

Next, a fifth embodiment of the invention is described. FIG. 13 shows a photoacoustic image generation apparatus of the fifth embodiment of the invention. An ultrasound unit 12a of a photoacoustic image generation apparatus 10a of this embodiment includes a transmission control circuit 33, a data separation means 34, an ultrasound image reconstruction means 35, a detection and logarithmic conversion means 36, an ultrasound image construction means 37 and an image combining means 38, in addition to the configuration of the ultrasound unit 12 of the photoacoustic image generation apparatus 10 of the first embodiment shown in FIG. 4. The difference between the photoacoustic image generation apparatus 10a of this embodiment and the photoacoustic image generation apparatus 10 of the first embodiment lies in that the photoacoustic image generation apparatus 10a generates an ultrasound image in addition to the photoacoustic image. It should be noted that, although ultrasound is used as the acoustic wave in this embodiment, the acoustic wave may be an acoustic wave of an audible frequency, which is appropriately selected depending on the subject to be examined, measurement conditions, etc. Further, this embodiment may be combined with any of the second to fourth embodiments to generate an ultrasound image in these embodiments.

In this embodiment, the probe 11 outputs (transmits) an acoustic wave (ultrasound) to the subject and detects (receives) reflected ultrasound of the transmitted ultrasound from the subject, in addition to detecting the photoacoustic signal. When an ultrasound image (reflected acoustic wave image) is generated, the trigger control circuit 29 sends an ultrasound transmission trigger signal, which instructs to transmit ultrasound, to the transmission control circuit 33. In response to the trigger signal, the transmission control circuit 33 causes the probe 11 to transmit ultrasound. After the ultrasound is transmitted, the probe 11 detects the reflected ultrasound from the subject. The transmission and the reception of ultrasound may be separated. For example, ultrasound may be transmitted from a position different from the position of the probe 11, and the probe 11 may receive the reflected ultrasound of the transmitted ultrasound.

The reflected ultrasound detected by the probe 11 is inputted to the AD conversion means 22 via the receiver circuit 21. The trigger control circuit 29 transmits a sampling trigger signal to the AD conversion means 22 in time with the transmission of ultrasound to start sampling of the reflected ultrasound. It should be noted that the reflected ultrasound travels back and forth between the probe 11 and a position at which the ultrasound is reflected; whereas the photoacoustic signal travels one way from a position at which it is generated to the probe 11. The detection of the reflected ultrasound takes twice the time taken for detection of the photoacoustic signal that is generated at the same depth position as the reflected ultrasound. Therefore, a sampling clock of the AD conversion means 22 may, for example, be 20 MHz, which is a half the sampling clock for sampling the photoacoustic signal. The AD conversion means 22 stores the sampled data of the reflected ultrasound in the reception memory 23. Either of the detection (sampling) of the photoacoustic signal or the detection (sampling) of the reflected ultrasound detect (sampling) may be performed first.

The data separation means 34 separates the sampled data of the photoacoustic signal and the sampled data of the reflected ultrasound stored in the reception memory 23 from one another. The data separation means 34 inputs the separated sampled data of the photoacoustic signal to the photoacoustic image reconstruction means 24. Generation of the photoacoustic image (absorption distribution image) involving deconvolution of the light pulse differential waveform is the same as that of the first embodiment. The data separation means 34 inputs the separated sampled data of the reflected ultrasound to the ultrasound image reconstruction means 35.

The ultrasound image reconstruction means 35 generates data of each line of an ultrasound image based on the reflected ultrasound (the sampled data thereof) detected with the ultrasound transducers of the probe 11. To generate the data of each line, a delay-and-sum method, etc., may be used, similarly to the generation of the data of each line by the photoacoustic image reconstruction means 24. The detection and logarithmic conversion means 36 finds an envelope of the data of each line outputted by the ultrasound image reconstruction means 35 and applies logarithmic conversion to the found envelope.

The ultrasound image construction means 37 generates an ultrasound image based on the data of each line after logarithmic conversion. The ultrasound image reconstruction means 35, the detection and logarithmic conversion means 36 and the ultrasound image construction means 37 form an ultrasound image generating means (reflected acoustic wave image generating means) for generating an ultrasound image based on the reflected ultrasound. The image combining means 38 combines the photoacoustic image and the ultrasound image with each other. For example, the image combining means 38 combines the images by superimposing the photoacoustic image and the ultrasound image one on the other. The thus generated composite image is displayed on the image display means 14. Alternatively, the photoacoustic image and the ultrasound image may not be combined and may be displayed side by side or one after the other on the image display means 14.

In this embodiment, the photoacoustic image generation apparatus generates the ultrasound image in addition to the photoacoustic image. By referencing the ultrasound image, portions that cannot be imaged in the photoacoustic image can be observed. The point that the absorption distribution can be imaged by deconvolving the light pulse differential waveform is the same as that in the first embodiment. Further, there are practical advantages, such that most part of algorithms for the image reconstruction, the detection and logarithmic conversion, etc., can be used both for generating the ultrasound image and generating the photoacoustic image and this allows simplification of a FPGA circuit configuration and software.

Figure 14:
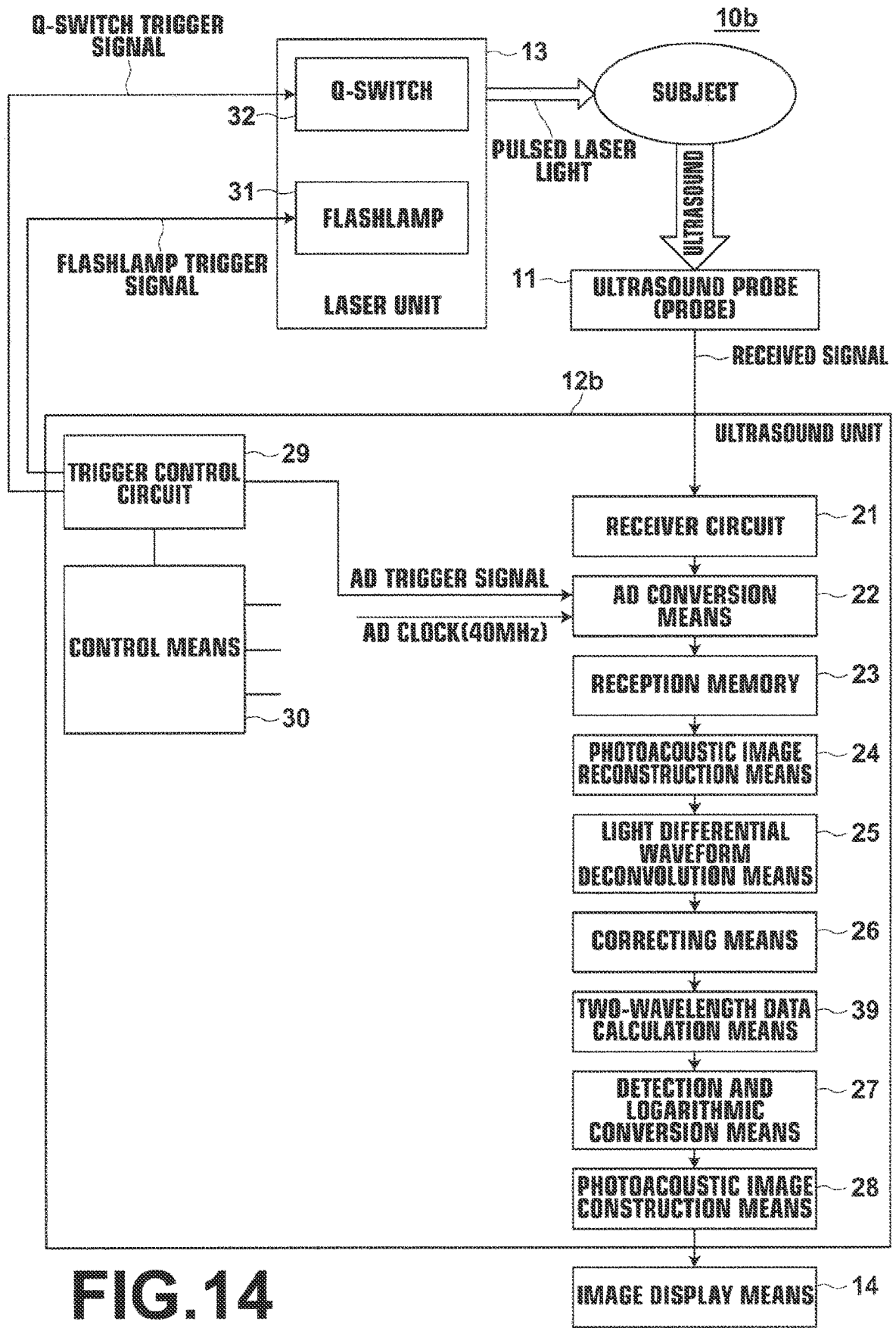
FIG. 14 is a block diagram illustrating a photoacoustic image generation apparatus of a sixth embodiment of the invention.

Next, a sixth embodiment of the invention is described. FIG. 14 shows a photoacoustic image generation apparatus of the sixth embodiment of the invention. This embodiment differs from the first embodiment in that a plurality of wavelengths of light are applied to the subject. An ultrasound unit 12b of a photoacoustic image generation apparatus 10b of this embodiment includes a two-wavelength data calculation means 39, which calculates photoacoustic signals (photoacoustic images) with respect to the plurality of wavelengths of light, in addition to the configuration of the ultrasound unit 12 of the photoacoustic image generation apparatus 10 of the first embodiment shown in FIG. 4. It should be noted that this embodiment may be combined with any of the second to fifth embodiments to apply a plurality of wavelengths of light to the subject and calculate photoacoustic signals (photoacoustic images) with respect to the plurality of wavelengths of light in these embodiments.

In this embodiment, the laser unit 13 is configured to be capable of switchably outputting one of the plurality of wavelengths of light. For example, the laser unit 13 switchably outputs one of pulsed laser light of a wavelength of 750 nm and pulsed laser light of a wavelength of 800 nm. After the pulsed laser light of each wavelength is outputted, the probe 11 detects a photoacoustic signal from the subject, and sampled data of the photoacoustic signal corresponding to the wavelength is stored in the reception memory 23. The stored photoacoustic signal corresponding to each wavelength is reconstructed by the photoacoustic image reconstruction means.

After the reconstruction by the photoacoustic image reconstruction means 24, the light differential waveform deconvolution means 25 deconvolves, from the photoacoustic signal (photoacoustic image) corresponding to each wavelength, a differential waveform (light differential waveform) of a temporal waveform of light intensity of the light of the wavelength applied to the subject. The photoacoustic signal from which the light differential waveform corresponding to each wavelength has been deconvolved is corrected by the correcting means 26, and then is processed by the two-wavelength data calculation means 39.

It should be noted that light absorption characteristics of many of living body tissues change depending on the wavelength of light, and each tissue has unique light absorption characteristics, in general. For example, the molecular absorption coefficient of oxygenated hemoglobin (hemoglobin bound with oxygen: oxy-Hb), which is rich inhuman arteries, at the wavelength of 750 nm is lower than the molecular absorption coefficient at the wavelength of 800 nm. On the other hand, the molecular absorption coefficient of deoxygenated hemoglobin (hemoglobin not bound with oxygen: deoxy-Hb), which is rich in veins, at the wavelength of 750 nm is higher than the molecular absorption coefficient at the wavelength of 800 nm. Utilizing these characteristics, a photoacoustic signal from an artery and a photoacoustic signal from a vein can be discriminated by checking whether the photoacoustic signal obtained at the wavelength of 750 nm is greater or smaller than the photoacoustic signal obtained at the wavelength of 800 nm.

The two-wavelength data calculation means 39 compares, for example, the magnitudes of the photoacoustic signals corresponding to the plurality of wavelengths relative to each other. Specifically, the two-wavelength data calculation means 39 compares the photoacoustic signal that is detected when the light of the wavelength of 750 nm is applied and the photoacoustic signal that is detected when the light of the wavelength of 800 nm is applied to check which signal is how much greater than the other signal. When the image is displayed, if the photoacoustic signal that is detected when the light of the wavelength of 750 nm is applied is greater than the other signal, it can be determined that the photoacoustic signal is one from a vein, and that portion may be displayed in blue. On the other hand, if the photoacoustic signal that is detected when the light of the wavelength of 800 nm is applied is greater than the other signal, it can be determined that the photoacoustic signal is one from an artery, and that portion may be displayed in red. It should be noted that the correcting means 26 may be omitted, as explained as to the first embodiment.

In this embodiment, after the deconvolution of the light differential waveform, the two-wavelength data calculation means 39 calculates the photoacoustic signals corresponding to the plurality of wavelengths. In the case where a plurality of wavelengths of light are applied to the subject where, for example, the light of the first wavelength is applied to the subject and a photoacoustic signal is detected and then the light of the second wavelength is applied to the subject and a photoacoustic signal is detected, there may be positional misalignment between the signals corresponding to the plurality of wavelengths due to influence of body motion, etc. When photoacoustic signals corresponding to a plurality of wavelengths are compared with each other, it is preferable to compare photoacoustic signals that are generated from the same point. In a case where the light differential waveform is not deconvolved, one blood vessel may be shown doubled, as shown in FIG. 3A, and it is difficult to confirm the position of each blood vessel during image interpretation and correct positional misalignment. By deconvolving the light differential waveform, the light absorption distribution can be imaged, as shown in FIG. 3B, and it is easier to confirm the position of each blood vessel and correct positional misalignment.

Further, in the case where one blood vessel is shown doubled, as shown in FIG. 3A, there is no signal at points corresponding to the interior of the blood vessel (the signal level is lower than a predetermined level). Therefore, if there is positional misalignment between the images corresponding to the plurality of wavelengths, the number of points where corresponding signals are present, i.e., overlapping points of the blood vessel, is decreased. In this case, it is difficult to appropriately compare the magnitudes of the photoacoustic signals corresponding to the plurality of wavelengths with each other. In contrast, in the case where the light absorption distribution is imaged, as shown in FIG. 3B, signals are present at many points in the blood vessel, and there are many overlapping points between the images corresponding to the plurality of wavelengths even when there is some positional misalignment. Therefore, in this embodiment, influence of positional misalignment can be reduced even when the images are compared with each other without aligning the images.

It should be noted that, although the photoacoustic signal and the light pulse differential waveform are converted into frequency domain signals, and are then converted back into time domain signals after the deconvolution in the frequency domain in the above-described embodiments, this is not intended to limit the invention. It is possible to perform the deconvolution of the light pulse differential waveform in the time domain. Further, the light differential waveform deconvolution means 25 may perform processing to apply some kind of filter to the photoacoustic signal when it performs the deconvolution. For example, the light differential waveform deconvolution means 25 may filter a noise-amplified frequency band when it performs the deconvolution.

In the above-described embodiments, a photoacoustic image (absorption distribution image) is generated after the light differential waveform is deconvolved from the photoacoustic signal. In addition, or alternatively, a photoacoustic image (pressure distribution image) may be generated without deconvolving the light differential waveform. For example, it may be configured such that the user can select, via operation of a switch or operation on the display monitor, whether or not to perform the deconvolution. Then, if the user has selected to perform the deconvolution, a photoacoustic image may be generated after deconvolving the light differential waveform, or if the user has selected not to perform the deconvolution, a photoacoustic image may be generated without performing the deconvolution of the light differential waveform. For example, in the case where the deconvolution of the light differential waveform is performed, the photoacoustic image may be displayed with associating the signal values to red and black colors, and in the case where the deconvolution of the light differential waveform is not performed, the photoacoustic image may be displayed with associating the signal values to blue and black colors.

Further, a photoacoustic image that is generated without performing the deconvolution may be analyzed with a computer to determine whether there is a blood vessel portion split into two. Then, if it is determined that there is a blood vessel portion split into two, the deconvolution of the light differential waveform may be performed only on the blood vessel portion. In this case, the blood vessel portion having been subjected to the deconvolution may be displayed in a different color from other blood vessel portions that have not been subjected to the deconvolution to facilitate discrimination between the blood vessel that has been subjected to the deconvolution and the other blood vessels that have not been subjected to the deconvolution.

The present invention has been described based on preferred embodiments thereof. However, the device and method for processing photoacoustic signals of the invention are not limited to the above-described embodiments, and modifications and variations made to the above-described embodiments are also within the scope of the invention.

What is claimed is:

1. A photoacoustic image generation apparatus comprising:
   a light source that applies a light to a subject according to a light intensity signal I(t);
   an ultrasound probe that detects a photoacoustic signal generated in the subject; and
   a photoacoustic signal processing circuitry that is configured to:
      obtain a light differential waveform I'(t) by differentiating the light intensity signal I(t) in time according to a formula I'(t)=d/dt I(t), the light differential waveform being a differential waveform of a temporal wave form of light intensity of the light applied to the subject;
      apply a first Fourier transform to the photoacoustic signal to obtain a Fourier transformed photoacoustic signal;
      apply a second Fourier transform to the light differential waveform to obtain a Fourier transformed light differential waveform;
      calculate a reciprocal of the Fourier transformed light differential waveform to obtain an inverse filter;
      apply the inverse filter to the Fourier transformed photoacoustic signal to obtain a filtered signal; and
      apply an inverse Fourier transform to the filtered signal to obtain a light absorption distribution of the subject.

2. The photoacoustic image generation apparatus as claimed in claim 1, wherein the photoacoustic signal is a sampled photoacoustic signal, and wherein the light differential waveform is a signal obtained by sampling the light differential waveform at a predetermined rate.

3. The photoacoustic image generation apparatus as claimed in claim 2, wherein the photoacoustic signal is sampled at a first sampling rate and the light differential waveform is sampled at a second sampling rate that is higher than the first sampling rate, and the photoacoustic signal processing circuitry is further configured to:
resample at the second sampling rate the photoacoustic signal sampled at the first sampling rate to create a resampled photoacoustic signal, and
wherein the first Fourier transform is applied to the resampled photoacoustic signal.

4. The photoacoustic image generation apparatus as claimed in claim 3, wherein the first Fourier transform and the second Fourier transform are applied using the same number of data points.

5. The photoacoustic image generation apparatus as claimed in claim 2, wherein the photoacoustic signal is sampled at a first sampling rate, the light differential waveform is sampled at a second sampling rate higher than the first sampling rate, the first Fourier transform is applied using a first number of data points, and the second Fourier transform is applied using a second number of data points greater than the first number of data points, and the photoacoustic signal processing circuitry is further configured to:
perform on the Fourier transformed photoacoustic signal, zero padding to add 0's of a number corresponding to a difference between the first number of data points and the second number of data points at the center of the Fourier transformed photoacoustic signal to create a zero-padded Fourier transformed photoacoustic signal, and
wherein the inverse filer is applied to the zero-padded Fourier transformed photoacoustic signal.

6. The photoacoustic image generation apparatus as claimed in claim 2, wherein the photoacoustic signal is sampled at a first sampling rate, the light differential waveform is sampled at a second sampling rate higher than the first sampling rate, the first Fourier transform is applied using a first number of data points, and the second Fourier transform is applied using a second number of data points greater than the first number of data points, and the photoacoustic signal processing circuitry is further configured to:
remove, from the Fourier transformed light differential waveform, high frequency component sample points of a number corresponding to a difference between the first number of data points and the second number of data points, and
calculate, as the inverse filter, a reciprocal of a signal obtained by removing the high frequency component sample points from the Fourier transformed light differential waveform.

7. The photoacoustic image generation apparatus as claimed in claim 5, wherein the second number of data points is a number of data points calculated by multiplying the first number of data points by a ratio of the second sampling rate to the first sampling rate.

8. The photoacoustic image generation apparatus as claimed in claim 3, wherein a sampling interval of the photoacoustic signal is longer than a pulse duration of the light applied to the subject.

9. The photoacoustic image generation apparatus as claimed in claim 1, wherein the photoacoustic signal processing circuitry is further configured to:
reconstruct a photoacoustic signal that is detected with a plurality of detector elements and sampled based on the photoacoustic signal; and
obtain the light absorption distribution of the subject based on the reconstructed photoacoustic signal and the light differential waveform.

10. The photoacoustic image generation apparatus as claimed in claim 1, wherein the photoacoustic signal processing circuitry is further configured to:
correct the photoacoustic signal such that influence of reception angle-dependent properties of a detector detecting the photoacoustic signal is removed.

11. The photoacoustic image generation apparatus as claimed in claim 1, wherein the photoacoustic signal processing circuitry is further configured to:
correct the photoacoustic signal such that influence of an incoming light distribution on the subject is removed.

12. The photoacoustic image generation apparatus as claimed in claim 1, wherein the photoacoustic signal processing circuitry is further configured to:
filter a noise-amplified frequency band.

13. The photoacoustic image generation apparatus as claimed in claim 1, wherein the light applied to the subject comprises a plurality of wavelengths of light, and the photoacoustic signal processing circuitry is further configured to:
sample a photoacoustic signal corresponding to light of each wavelength; and
obtain the light absorption distribution of the subject based on the sampled photoacoustic signal corresponding to the light of each wavelength and the light differential waveform.

14. The photoacoustic image generation apparatus as claimed in claim 1, wherein the photoacoustic signal processing circuitry is further configured to generate a photoacoustic image based on the light absorption distribution of the subject using the light differential waveform.

15. The photoacoustic image generation apparatus as claimed in claim 14, wherein the photoacoustic signal processing circuitry is further configured to:
sample a reflected acoustic wave of an acoustic wave transmitted to the subject;
generate a reflected acoustic wave image based on the sampled reflected acoustic wave; and
combine the photoacoustic image with the reflected acoustic wave image.

16. The photoacoustic image generation apparatus as claimed in claim 15, wherein the photoacoustic signal processing circuitry is further configured to combine the images by superimposing the photoacoustic image and the reflected acoustic wave image one on the other.

17. A photoacoustic signal processing method comprising the steps of:
applying light to a subject using the light source according to a light intensity signal I(t);
detecting, using an ultrasound probe, a photoacoustic signal generated in the subject due to the light applied to the subject; and
using a photoacoustic signal processing circuitry to
calculate a light differential waveform I'(t) by differentiating the light intensity signal I(t) in time according to a formula I'(t)=d/dt I(t), the light differential waveform being a differential waveform of a temporal wave form of light intensity of the light applied to the subject,
apply a first Fourier transform to the photoacoustic signal to obtain a Fourier transformed photoacoustic signal;

apply a second Fourier transform to the light differential waveform to obtain a Fourier transformed light differential waveform;

calculate a reciprocal of the Fourier transformed light differential waveform to obtain an inverse filter;

apply the inverse filter to the Fourier transformed photoacoustic signal to obtain a filtered signal;

apply an inverse Fourier transform to the filtered signal to obtain a light absorption distribution of the subject.

18. The photoacoustic signal processing method as claimed in claim 17, wherein the photoacoustic signal is a sampled photoacoustic signal, and wherein the light differential waveform is a signal obtained by sampling the light differential waveform at a predetermined rate.

19. The photoacoustic signal processing method as claimed in claim 17, further comprising generating a photoacoustic image based on the signal based on the light absorption distribution using the light differential waveform.

* * * * *